US011872256B2

(12) United States Patent
Dubar et al.

(10) Patent No.: US 11,872,256 B2
(45) Date of Patent: Jan. 16, 2024

(54) BACTERIOPHAGE COMPOSITION AND METHOD OF PREVENTING BACTERIAL INFECTIONS IN LIVESTOCK

(71) Applicant: SYNTBIOLAB INC., Lévis (CA)

(72) Inventors: Rodrigue Dubar, Québec (CA); Simon Labrie, Québec (CA)

(73) Assignee: SYNTBIOLAB INC., Lévis (CA)

( * ) Notice: Subject to any disclaimer, the term of this patent is extended or adjusted under 35 U.S.C. 154(b) by 628 days.

(21) Appl. No.: 16/647,445

(22) PCT Filed: Sep. 14, 2018

(86) PCT No.: PCT/CA2018/051141
§ 371 (c)(1),
(2) Date: Mar. 13, 2020

(87) PCT Pub. No.: WO2019/051603
PCT Pub. Date: Mar. 21, 2019

(65) Prior Publication Data
US 2021/0008133 A1 Jan. 14, 2021

Related U.S. Application Data

(60) Provisional application No. 62/558,924, filed on Sep. 15, 2017.

(51) Int. Cl.
*A61K 35/76* (2015.01)
*A23K 10/18* (2016.01)
*A61P 31/04* (2006.01)
*C12N 7/00* (2006.01)

(52) U.S. Cl.
CPC .............. *A61K 35/76* (2013.01); *A23K 10/18* (2016.05); *A61P 31/04* (2018.01); *C12N 7/00* (2013.01); *C12N 2795/00032* (2013.01); *C12N 2795/00051* (2013.01)

(58) Field of Classification Search
None
See application file for complete search history.

(56) References Cited

U.S. PATENT DOCUMENTS

2016/0030495 A1 2/2016 Serwer

FOREIGN PATENT DOCUMENTS

| CN | 104994740 A | 10/2015 |
|---|---|---|
| CN | 105308179 A | 2/2016 |
| CN | 106574251 A | 4/2017 |

OTHER PUBLICATIONS

Carvalho, C.M., et al., The in vivo efficacy of two administration routes of a phage cocktail to reduce numbers of *Campylobacter coli* and *Campylobacter jejuni* in chickens. BMC Microbiol. 2010. vol. 10, 232, pp. 1-11.
Chan, B.K., et al., Phage cocktails and the future of phage therapy. Future Microbiol. 2013., vol. 8, No. 6, pp. 769-683.
Clark, J. R. et al., Bacteriophages and biotechnology: vaccines, gene therapy and antibacterials. Trends Biotechnology 2006, vol. 24, 5. pp. 212-218.
Clavijo, V., et al., The gastrointestinal microbiome and its association with the control of pathogens in broiler chicken production: a review. 2018. Poult. Sci., vol. 93, No. 3, pp. 1006-1021.
Costa, J. Increased production of biofilms by *Escherichia coli* in the presence of enrofloxacin. 2012. vol. 45(9), pp. 1076-1085.
Del Casale, A., et al., Extent and variation of phage-borne bacterial 16S rRNA gene sequences in wastewater environments. 2011. Appl. Environ. Microbiol., vol. 77, No. 15, pp. 5529-5532.
Hamdi, S., et al., Characterization of five Podoviridae phages infecting *Citrobacter freundii*. 2016. Front. Microbiol., vol. 7, Article 1023, pp. 1-18.
Huff, W. E. et al., Bacteriophage Treatment of a Severe *Escherichia coli* Respiratory Infection in Broiler Chickens. 2003. Avian Diseases, vol. 47, pp. 1399-1405.
Johnson, R. P. et al., Bacteriophages for prophylaxis and therapy in cattle, poultry and pigs. 2008. Animal Health Research Reviews, vol. 9, pp. 201-215.
Kutter, E. et al., Phage Therapy in Clinical Practice: Treatment of Human Infections. 2010. Current Pharmaceutical Biotechnology, 11, pp. 69-86.
Labrie, S. J., et al., Bacteriophage resistance mechanisms. 2010. Nat. Rev. Microbiol., vol. 9, pp. 317-327.
Oliveira, A., et al., In vivo efficiency evaluation of a phage cocktail in controlling severe colibacillosis in confined conditions and experimental poultry houses. 2010. Vet. Microbiol., vol. 146, pp. 303-308.
Saini, V. et al., Antimicrobial resistance profiles of common mastitis pathogens on Canadian dairy farms. 2012. Journal of Dairy Science, vol. 95, pp. 4319-4332.
Summers, W. C. et al., Bacteriophage Therapy. 2001. Annual Review of Microbiology, vol. 55, pp. 437-451.
Weber-Dabrowska, B., et al., Bacteriophage procurement for therapeutic purposes. 2016. Front. Microbiol., vol. 7, Article 1177, pp. 1-14.
Liao, W. et al., "T4-Like Genome Organization of the *Escherichia coli* 0157:H7 Lytic Phage AR1," Journal of Virology, vol. 85; No. 13; 6567-6578 (2011).
Lupo, D. et al., "The T7 ejection nanomachine components gp15-gp16 form a spiral ring complex that binds DNA and a lipid membrane," Virology, vol. 486; 263-271 (2015).
Maffei, E. et al., "Systematic exploration of *Escherichia coli* phage-host interactions with the BASEL phage collection," Institute of Medical Microbiology, University of Zürich, Zürich, Switzerland; 79 pages (2021).
McPartland J. and Rothman-Denes, L.B., "The Tail Sheath of Bacteriophage N4 Interacts with the *Escherichia coli* Receptor," Journal of Bacteriology, vol. 191; No. 2; 525-532 (2009).

(Continued)

*Primary Examiner* — Jennifer E Graser
(74) *Attorney, Agent, or Firm* — Hamilton, Brook, Smith & Reynolds, P.C.

(57) ABSTRACT

The present invention provides new bacteriophages, their selection, compositions, cocktails and formulations thereof, and their administration for the prevention of opportunistic infections in livestock, such as Avian Pathogenic *E. Coli* (APEC) infections in poultry.

18 Claims, 12 Drawing Sheets

Specification includes a Sequence Listing.

(56) References Cited

OTHER PUBLICATIONS

Yu, F. and Mizushima, S., "Roles of Lipopolysaccharide and Outer Membrane Protein OmpC of *Escherichia coli* K-12 in the Receptor Function for Bacteriophage T4," Journal of Bacteriology, vol. 151; No. 2; 718-722 (1982).

Kebede, F., "Pseudomonas infection in chickens," Journal of Veterinary Medicine and Animal Health, vol. 2; No. 4; 55-58 (2010).

Merabishvili, M. et al., "Quality-Controlled Small-Scale Production of a Well-Defined Bacteriophage Cocktail for Use in Human Clinical Trials," PLOS One, vol. 4; No. 3; e4944; 10 pages (2009).

Oliveira, A. et al., "In vivo efficiency evaluation of a phage cocktail in controlling severe colibacillosis in confined conditions and experimental poultry houses," Veterinary Medicine, vol. 146; 303-308 (2010).

Silva, J.B. et al., "Host receptors for bacteriophage adsorption," FEMS Microbiology Letters, vol. 363; 11 pages (2016).

Extended European Search Report issued in EP Application No. 18856077.5, entitled: "Bacteriophage Composition and Method of Preventing Bacterial Infections in Livestock," dated May 6, 2021; 12 pages.

Supplementary European Search Report issued in EP Application No. 18856077.5, entitled: "Bacteriophage Composition and Method of Preventing Bacterial Infections in Livestock," dated May 26, 2021; 1 page.

International Preliminary Report on Patentability for International Application No. PCT/CA2018/051141, entitled: "Bacteriophage Composition And Method Of Preventing Bacterial Infections In Livestock," date completed: Dec. 19, 2019.

International Search Report and Written Opinion for International Application No. PCT/CA2018/051141, entitled: "Bacteriophage Composition And Method Of Preventing Bacterial Infections In Livestock," dated Nov. 30, 2018.

Brown, P.K. and Curtis, R., "Unique chromosomal regions associated with virulence of an avian pathogenic *Escherichia coli* strain," Proc. Natl. Acad. Sci., vol. 93; 11149-11154 (1996).

Gaukler, S.M. et al., "*Escherichia coli, Salmonella,* and *Mycobacterium avium* subsp. *paratuberulosis* in Wild European Starlings at a Kansas Cattle Feedlot," Avian Diseases, vol. 53; 544-551 (2009).

Gill, J.J. and Hyman, P., "Phage Choice, Isolation, and Preparation for Phage Therapy," Current Pharmaceutical Biotechnology, vol. 11; 2-14 (2010).

Wyrsch, E. et al., "Comparative genomic analysis of a multiple antimicrobial resistant enterotoxigenic *E. coli* O157 lineage from Australian Pigs," BMC Genomics, vol. 16; 165; 11 Pages (2015).

Xing-Shu, M. et al., "Research Progress on Avian Pathogenic *Escherichia coli,*" Animal Husbandry and Veterinary in China, Issue 2, 169-174 (2013)—English Abstract Attached, only reviewed English abstract; full text no translation.

| | APEC-A | APEC-B | APEC-C | APEC-D | APEC-E | APEC-F | X7122 | Poulvac |
|---|---|---|---|---|---|---|---|---|
| 1 | 3 | 0 | 0 | 0 | 0 | 0 | 3 | 0 |
| 2 | 3 | 0 | 0 | 0 | 0 | 0 | 3 | 0 |
| 3 | 3 | 0 | 0 | 0 | 0 | 0 | 3 | 0 |
| 4 | 0 | 3 | 0 | 0 | 0 | 0 | 0 | 0 |
| 5 | 0 | 3 | 0 | 3 | 0 | 0 | 0 | 0 |
| 6 | 0 | 3 | 0 | 3 | 0 | 0 | 0 | 0 |
| 7 | 0 | 3 | 0 | 3 | 0 | 0 | 0 | 0 |
| 8 | 0 | 3 | 0 | 3 | 3 | 0 | 1 | 0 |
| 9 | 0 | 3 | 0 | 3 | 0 | 0 | 0 | 0 |
| 10 | 0 | 0 | 0 | 0 | 0 | 0 | 0 | 0 |
| 11 | 0 | 2 | 3 | 0 | 0 | 0 | 0 | 0 |
| 12 | 0 | 3 | 0 | 3 | 0 | 0 | 0 | 0 |
| 13 | 0 | 3 | 0 | 0 | 0 | 0 | 0 | 0 |
| 14 | 0 | 3 | 0 | 0 | 0 | 0 | 0 | 0 |
| 15 | 0 | 3 | 0 | 0 | 0 | 0 | | 0 |
| 16 | 0 | 3 | 0 | 1 | 0 | 0 | 0 | 0 |
| 17 | 0 | 0 | 2 | 0 | 0 | 0 | 0 | 0 |
| 18 | 0 | 0 | 2 | 0 | 0 | 0 | 0 | 0 |
| 19 | 0 | 0 | 2 | 0 | 0 | 0 | 0 | 0 |
| 20 | 0 | 0 | 2 | 0 | 0 | 0 | 0 | 0 |
| 21 | 0 | 0 | 3 | 0 | 0 | 0 | 0 | 0 |
| 22 | 0 | 0 | 3 | 0 | 0 | 0 | 0 | 0 |
| 23 | 0 | 0 | 3 | 0 | 0 | 0 | 0 | 0 |
| 24 | 3 | 3 | 3 | 3 | 0 | 3 | 3 | 2 |
| 25 | 1 | 3 | | | 0 | 3 | 3 | 3 |
| 26 | 3 | 3 | | | 0 | 3 | 3 | 3 |
| 27 | 0 | 0 | 1 | | 0 | 0 | 0 | 0 |
| 28 | 3 | 3 | 3 | | 0 | 3 | 3 | 3 |
| 29 | 3 | 3 | 3 | | 0 | 3 | 3 | 3 |
| 30 | 3 | 3 | 3 | | 0 | 3 | 3 | 3 |
| 31 | 0 | 3 | 3 | | 0 | 0 | 0 | 0 |
| 32 | 3 | 3 | 3 | | 0 | 3 | 3 | |
| 33 | 2 | 3 | 0 | | 3 | 0 | 0 | 3 |
| 34 | 0 | 3 | 0 | | 1 | 0 | 0 | 0 |
| 35 | 0 | 3 | 0 | 3 | 0 | 0 | 0 | 0 |
| 36 | 0 | 3 | 0 | 3 | 0 | 0 | 0 | 0 |
| 37 | 0 | 3 | 0 | 3 | 0 | 0 | 0 | 0 |
| 38 | 0 | 3 | 0 | 3 | 3 | 0 | 0 | 0 |
| 39 | 3 | 3 | 0 | 3 | 3 | 0 | 0 | 3 |
| 40 | 0 | 3 | 0 | 3 | 1 | 0 | 0 | 0 |
| 41 | 0 | 2 | 0 | | 0 | 0 | 0 | 0 |
| 42 | 3 | 2 | 0 | | 2 | 0 | 2 | 3 |
| 43 | 3 | 2 | 0 | 1 | 2 | 0 | 2 | 3 |
| 44 | 0 | 2 | 0 | 1 | 0 | 0 | 0 | 0 |
| 45 | 3 | | 0 | 1 | 3 | 0 | 2 | 3 |
| 46 | 3 | | 0 | 1 | 3 | 0 | 2 | 3 |
| 47 | 3 | | 0 | 1 | 3 | 0 | 2 | 3 |
| 48 | 3 | | 0 | 1 | 3 | 0 | 2 | 3 |
| 49 | 1 | | 0 | | 3 | 0 | 1 | 2 |
| 50 | 3 | | 0 | | 3 | 0 | 1 | 2 |

*Figure 7*

BACTERIOPHAGE COMPOSITION AND METHOD OF PREVENTING BACTERIAL INFECTIONS IN LIVESTOCK

This application is a national stage application under 35 U.S.C. § 371 of International Application No. PCT/CA2018/051141, filed Sep. 14, 2018, entitled "Bacteriophage Composition and Method of Preventing Bacterial Infections in Livestock," which claims priority to U.S. Provisional Patent Application No. 62/558,924, filed Sep. 15, 2017, the contents of all of which are hereby incorporated herein in their entirety by reference for all purposes.

SEQUENCE LISTING

The instant application contains a Sequence Listing, which has been submitted in ASCII format via EFS-Web, and is hereby incorporated by reference in its entirety. Said ASCII copy is named "20200527_Amended_Sequence_Listing_18385_6_ST25.txt", and is 5,291,869 bytes in size.

FIELD OF THE INVENTION

The present invention relates to a composition comprising bacteriophages and its use for the prevention of bacterial infections, namely for the substitution of antibiotherapy in livestock, such as poultry or pigs.

BACKGROUND OF THE INVENTION

Infections of livestock cause tens of billions of dollars of losses per year, including 5-10 billion dollars from food-borne illness. These infections are primarily caused by six pathogens, *Salmonella enterica*, *Listeria monocytogenes*, *Escherichia coli* (such as APEC or ExPEC), *Campylobacter jejuni*, *Staphylococcus aureus* and *Clostridium perfringens*.

Avian pathogenic *Escherichia coli* (APEC) strains cause systemic and localized infections in poultry, jointly termed colibacillosis. Avian colibacillosis is responsible for significant economic losses to the poultry industry due to disease treatment, decrease in growth rate and egg production, and mortality. APEC are also considered a potential zoonotic risk for humans. Designing successful strategies against their infections and their transmission is therefore a need for human health and economic viability of the industry.

Extraintestinal pathogenic *Escherichia coli* (ExPEC) possess virulence traits that allow it to invade, colonize, and induce disease in bodily sites outside of the gastrointestinal tract. Human diseases caused by ExPEC include urinary tract infections, neonatal meningitis, sepsis, pneumonia, surgical site infections, as well as infections in other extraintestinal locations. ExPEC-induced diseases represent a large burden in terms of medical costs and productivity losses. In addition to human illnesses, ExPEC strains also cause extraintestinal infections in domestic animals and pets. A commonality of virulence factors has been demonstrated between human and animal ExPEC, suggesting that the organisms are zoonotic pathogens. ExPEC strains have been isolated from food products, particularly from raw meats and poultry, indicating that these organisms potentially represent a new class of foodborne pathogens.

Prior attempts with phage therapeutic have failed and modern approaches to these failures have now revealed that phages used for antibacterial therapies in certain specific situations are highly efficient, which makes this new type of treatment very attractive and useful. The bacteriophage preparations, however, must be so selected that virulent, non-toxic, host-specific cocktails are prepared.

Against such a background, there is a need to develop host-specific, non-toxic and virulent bacteriophage preparations that can be used to effectively prevent bacterial infections in livestock.

Embodiments of this invention are directed generally to disease prevention in livestock, particularly in the poultry industry. Certain aspects are directed to prophylactic compositions comprising bacteriophages and methods of using the same.

SUMMARY OF THE INVENTION

A main aspect intended to be addressed by the present invention is to provide phage prophylaxis implemented alone, or as a mixture of phages (cocktail). The phages in such a composition can be optimized for the bacteria targeted.

Alternatively, the use of a cocktail may maximize the range of bacterial targets and minimizes the emergence of bacterial resistance.

This invention relates to a method for preparing a strain of bacteriophage specific to selected opportunistic bacteria, bacteriophage strains obtained in this way and the application of bacteriophages to manufacture a preparation for preventing and fighting infections of livestock, especially poultry, with pathogenic strains of bacteria sensitive to these bacteriophages.

This invention helps provide a production technology for an antimicrobial preparation suitable for use as a food- or feed-additive for livestock, such as for example, poultry, beef and pigs, which at the same time is specific to opportunistic bacteria, such as for example, pathogenic strains of *E. coli* that cause incidence of disease or death.

The present invention helps provide a preparation that could replace the currently used antibiotics in livestock.

With the aim of providing an alternative source of antibacterial compositions for the prevention of opportunistic or pathogenic bacteria, there is provided an isolated bacteriophage (i.e. bacteriophage strain) specific against an opportunistic bacterial infection in livestock, wherein the bacteriophage has an absence of a gene coding for an integrase.

According to a particular embodiment, the bacteriophage strain further has at least one of: an absence of toxin gene; an absence of antibiotic resistance gene; and an absence of 16S RNA pathogenic gene marker.

According to a particular embodiment, the bacteriophage strain further has at least one of: a stability at a temperature between 4° C. and RT; a stability at pH 4; and a burst size greater than 10 against the opportunistic bacterial infection.

In accordance with a further aspect of the invention, there is provided a method for selecting a bacteriophage for preventing an opportunistic bacterial infection in livestock, the method comprising: a) isolating a plurality of bacteriophage strain from an environmental sample; b) characterizing the bacteriophage strain based on an absence of integrase gene, and optionally at least one of: bacterial host range; burst size; toxin gene; antibiotic resistance gene; and 16S RNA gene; c) selecting at least one of the characterized bacteriophage strain based on an absence of integrase gene, and optionally at least one criteria selected from: absence of toxin gene; absence of antibiotic resistance gene; and absence of 16S RNA pathogenic gene marker. Particularly, the method further comprises the selection of the bacteriophage based on at least one of: stability between 4° C. and RT; stability at pH 4; and a burst size greater than 10 against the opportunistic bacterial infection.

According to a particular embodiment, the method further comprises: c) selecting at least two of the characterized strain based on: having different or complementary host ranges against at least 2 different bacterial strain; and d) combining the at least two selected bacteriophage strain to form a cocktail.

In accordance with a particular aspect of the present invention, there is provided a cocktail comprising at least two bacteriophage strains as defined herein, having complementary host ranges against at least 2 different opportunistic bacterial strain.

DETAILED DESCRIPTION OF THE INVENTION

Description of the Figures

FIG. 4. Host range of a first set of phages against 35 APEC strain. The lysis efficiency was measured on a scale of 0 to 3 (0: no lysis, 1: turbid lysis, 2: partial lysis; and 3 complete lysis).

FIG. 5. Host range of a second set of phages against 8 APEC strain. The lysis efficiency was measured on a scale of 0 to 3 (0: no lysis, 1: turbid lysis, 2: partial lysis; and 3 complete lysis).

FIG. 7. Scheme illustrating the dilution methodology for precise titration of phages.

ABBREVIATONS AND DEFINITIONS

Abbreviations

Figure 1:
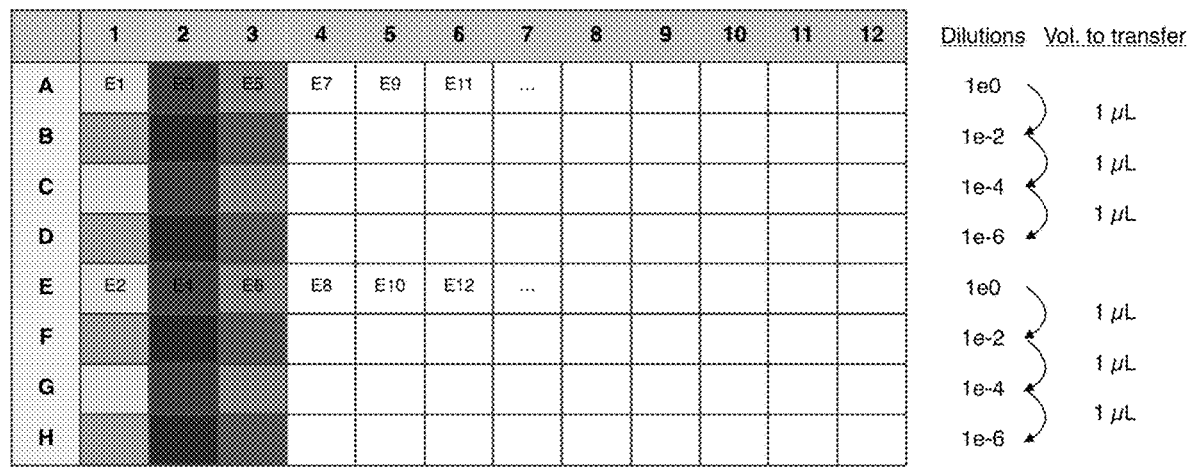
FIG. 1. Picture of dilution methodology for enrichment of phages.

APEC A: *Escherichia coli* QT217=*Escherichia coli* X7122; APEC B: *Escherichia coli* QT4438=*Escherichia coli* MT78; APEC C: *Escherichia coli* QT3694=*Escherichia coli* 598; APEC D: *Escherichia coli* QT2550=*Escherichia coli* TK3; APEC E: *Escherichia coli* QT2551=*Escherichia coli* CH9; APEC F: *Escherichia coli* CH14; 4805A: *Escherichia coli* 4805A; 4813A : *Escherichia coli* 4813A; 4824A: *Escherichia coli* 4824 A; 4806A: *Escherichia coli* 4806A; 4815A: *Escherichia coli* 4815A; 4817A: *Escherichia coli* 4817A; 4819A: *Escherichia coli* 4819A; 4821 A: *Escherichia coli* 4821 A; 4829: *Escherichia coli* 4829; 4818: *Escherichia coli* 4818; 4823A: *Escherichia coli* 4823A; 4828B: *Escherichia coli* 4828B; 4809A: *Escherichia coli* 4809A; 481 1 A: *Escherichia coli* 481 1 A; 4816A: *Escherichia coli* 4816A; 4825A: *Escherichia coli* 4825A; 4826A: *Escherichia coli* 4826A; 4831 A: *Escherichia coli* 4831 A; 4820A: *Escherichia coli* 4820A; 4832A: *Escherichia coli* 4832A; 4833A: *Escherichia coli* 4833A; 4830A: *Escherichia coli* 4830A; 4822: *Escherichia coli* 4822; 4812: *Escherichia coli* 4812; 4814A: *Escherichia coli* 4814A; 4827A: *Escherichia coli* 4827A; 4807A: *Escherichia coli* 4807A; 4808A: *Escherichia coli* 4808A; 481 OA: *Escherichia coli* 481 OA.

Definitions

As used herein the singular forms "a", "and", and "the" include plural referents unless the context clearly dictates otherwise. Thus, for example, reference to "a cell" includes a plurality of such cells and reference to "the culture" includes reference to one or more cultures and equivalents thereof known to those skilled in the art, and so forth. All technical and scientific terms used herein have the same meaning as commonly understood to one of ordinary skill in the art to which this invention belongs unless clearly indicated otherwise.

The terms "about" or "around" as used herein refers to a margin of +or −10% of the number indicated. For sake of precision, the term about when used in conjunction with, for example: 90% means 90% +/−9% i.e. from 81% to 99%. More precisely, the term about refers to +or −5% of the number indicated, where for example: 90% means 90% +/−4.5% i.e. from 86.5% to 94.5%. When used in the context of a pH, the term about means +/−0.5 pH unit.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, un-recited elements or method steps.

As used herein, the terms "disease" and "disorder" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

The term "subject" or "patient" as used herein refers to an animal, preferably a mammal, and most preferably a human who is the object of treatment, observation or experiment.

"Mammal" includes humans and both domestic animals such as laboratory animals and household pets, (e.g. cats, dogs, swine, cattle, sheep, goats, horses, rabbits), farm animals such as livestock, poultry etc. and non-domestic animals such as wildlife and the like.

The term "isolated" is used herein to indicate that the bacteriophage exists in a physical milieu distinct from that in which it occurs in nature. For example, the isolated phage may be substantially isolated (for example enriched or purified) with respect to the complex cellular milieu in which it naturally occurs, and other bacteriophage strain with which it is found in nature. In some circumstances, the isolated bacteriophage forms part of a composition (for example containing many other substances) or buffer system, which may for example contain other components.

The bacteriophages(s) described herein can be formulated as pharmaceutical compositions by formulating with carrier such as food- or feed-acceptable carrier, especially veterinary food- or feed-acceptable carriers or excipients, in particular, for poultry or chicks.

As used herein, the term "food- or feed-acceptable" refers to molecular entities and compositions that are physiologically tolerable and do not typically produce an allergic or similar unwanted reaction, such as gastric upset, dizziness and the like, when administered to mammals. Preferably, as used herein, the term "food- or feed-acceptable" means approved by regulatory agency of the federal or state government for use in mammals, and more particularly in poultry.

The term "carrier" refers to a diluent, adjuvant, excipient, or vehicle with which the compounds of the present invention may be administered. Sterile water or aqueous saline solutions and aqueous dextrose and glycerol solutions may be employed as carrier, particularly for injectable solutions. Suitable pharmaceutical carriers are described in "Remington's Pharmaceutical Sciences" by E. W. Martin.

The term "effective amount" means an amount effective, at dosages and for periods of time necessary, to achieve the desired therapeutic or prophylactic result. An "effective amount" of an anti-bacterial agent, in reference to decreasing bacterial cell growth, means an amount capable of decreasing, to some extent, the growth of targeted bacteria. The term includes an amount capable of invoking a growth inhibitory, cytostatic and/or cytotoxic effect and/or killing of targeted bacteria. Particularly, the term effective amount means a decrease by 10%, 20%, 30%, 40%, 50%, 60%, 70%, 80%, 90%, 95%, 98% and/or 99% of the original bacterial count.

The terms "inhibiting," "reducing," or "prevention," or any variation of these terms, when used in the claims and/or the specification includes any measurable decrease or complete inhibition to achieve a desired result. Particularly, the term "inhibiting" or "reducing" means a decrease by 10%, 20%, 30%, 40%, 50%, 60%, 70%, 80%, 90%, 95%, 98% and/or 99% of the original bacterial count.

DETAILED DESCRIPTION OF PARTICULAR ASPECTS OF THE INVENTION

Bacterial infections are most frequently treated by the administration of antibiotics. However, antibiotic treatment is sometimes not effective, especially when the infection is biofilm-based, and in some cases, antibiotics promote the formation of biofilms (Costa et al., *Vet Microbiol* (2012), 160, 488-90). Furthermore, the continued use of antibiotics over many years has led some of these bacteria to become resistant to multiple antibiotics (multi-antibiotic resistant) (Saini et al., *J Dairy Sci* (2012), 95, 4319-32).

Historically, antibiotic therapy was predicated by therapies that employed bacterial viruses (bacteriophages or phages) as agents to kill pathogenic bacteria (Summers, *Ann Rev Microbiol* (2001), 55:437-51; Huff et al., *Avian Diseases* (2003), 47:1399-1405; Johnson et al., Animal Health Res Rev (2008), 9:201-15; Clark and March, TRENDS Biotechnol (2006), 24:212-18; Kutter et al., *Curr Pharmaceut Biotechnol* (2012), 11:69-86). This phage therapy has also been used to treat farm and ranch animals such as chickens, hogs, and cattle (Summers, *Ann Rev Microbiol* (2001), 55:437-51; Huff et al., Avian Diseases (2003), 47:1399-1405; Johnson et al., *Animal Health Res Rev* (2008), 9:201-15). In some cases, for example in the treatment of typhoid fever, phage therapy was dramatically effective.

However, it was not always effective for treatment of farm/ranch animals or humans (Summers, *Ann Rev Microbiol* (2001), 55:437-51; Huff et al., Avian Diseases (2003), 47:1399-1405; Johnson et al., *Animal Health Res Rev* (2008), 9:201-15; Clark and March, *TRENDS Biotechnol* (2006), 24:212-18; Kutter et al., *Curr Pharmaceut Biotechnol* (2012), 11:69-86). Most early studies on phage therapy were not rigorously controlled.

Other than some isolated success with the treatment of *E. coli*-caused diarrhea in calves, advances in phage therapy have been incremental and largely disappointing. More effective phages are needed, more rapid methods for isolating and recognizing effective phages, and potentially, more effective multi-phage-containing cocktails. These methods must be combined to improve the phage therapy and prophylaxis of the infectious diseases of both farm and ranch animals.

In accordance with the needs identified herein, the present invention provides compositions directed to disease prevention in livestock, particularly in the poultry industry. Certain embodiments are directed to prophylactic compositions comprising bacteriophages and methods of using the same.

Selecting and Isolating Bacteriophage Strains

With the aim of providing an alternative source of anti-bacterial composition for the prevention of opportunistic or pathogenic bacteria, there is provided a method for manufacturing a bacteriophage/bacteriophage strain/bacteriophage composition for the prevention of an opportunistic bacterial infection in livestock, the method comprising: a) isolating a plurality of bacteriophages from an environmental sample, b) characterizing the bacteriophages based on absence or presence of an integrase gene; and c) selecting one or more bacteriophage strain having an absence of integrase gene for making the composition.

Thus, in accordance with a particular embodiment of the invention, there is provided an isolated bacteriophage strain specific against an opportunistic bacterial infection in livestock, wherein the bacteriophage strain has an absence of a gene coding for an integrase.

Further Selection of Bacteriophage Strains

In accordance with a further embodiment, the bacteriophage strain is further characterized by being at least one of: directed towards a plurality of bacterial hosts; and/or a burst size greater than 10.

In accordance with a further embodiment, the bacteriophage strain is further characterized by being at least one of: stable between about 4° C. and RT and stable at pH about 4.

In accordance with a particular embodiment of the invention, the bacteriophage is further characterized as having at least one of: an absence of toxin gene; an absence of antibiotic resistance gene; and an absence of 16S RNA gene marker.

Particularly, the bacteriophage is further characterized as having at least two of: a target pattern directed towards a plurality of bacterial hosts; a burst size greater than 10 against at least one of the bacterial hosts; an absence of toxin gene; an absence of antibiotic resistance gene; and an absence of 16S RNA gene marker; stability at a temperature between 4° C. and RT; and stability at pH 4.

More particularly, the isolated bacteriophage strain is characterized by: an absence of a gene coding for an integrase, and optionally as having at least three of: a target pattern directed towards a plurality of bacterial hosts; a burst size greater than 10 against at least one of the bacterial host; an absence of toxin gene; an absence of antibiotic resistance gene; and an absence of 16S RNA gene marker; stability at a temperature between 4° C. and RT; and stability at pH 4.

Most particularly, the isolated bacteriophage strain is characterized by: an absence of a gene coding for an integrase, and optionally as having all of: a target pattern directed towards a plurality of bacterial hosts; a burst size greater than 10 against at least one of the bacterial host; an absence of toxin gene; an absence of antibiotic resistance gene; and an absence of 16S RNA gene marker; stability at a temperature between 4° C. and RT; and stability at pH 4.

Still, most particularly, the isolated bacteriophage strain is characterized by: an absence of a gene coding for an integrase, and having all of: a target pattern directed towards a plurality of bacterial hosts; a burst size greater than 10 against at least one of the bacterial host; an absence of toxin gene; an absence of antibiotic resistance gene; and an absence of 16S RNA gene marker; and optionally, having: stability at a temperature between 4° C. and RT; and stability at pH 4.

Method for Production

Alternatively, there is provided a method for producing a bacteriophage/bacteriophage strain/bacteriophage composition for the prevention of an opportunistic bacterial infection in livestock, the method comprising: a) isolating a plurality of bacteriophage strain from an environmental sample; b) characterizing the bacteriophage strain based on at least one of: bacterial host range; burst size; toxin gene; antibiotic resistance gene; and 16S RNA gene; c) selecting at least one of the characterized bacteriophage strain based on at least two criteria selected from: i) absence of toxin gene; ii) absence of antibiotic resistance gene; and iii) absence of 16S RNA gene.

According to a particular embodiment, the method is carried out wherein the bacteriophage strain is further characterized and selected based on c) at least one criterium selected from: plurality of bacterial host; and a burst size greater than 10.

Particularly, the method further comprises: c) selecting at least two of the characterized bacteriophage strains based on having different or complementary host ranges against at least two different opportunistic bacterial strains; and d) combining the at least two selected bacteriophage strains to form a bacteriophage cocktail composition.

According to an alternative embodiment, there is provided the method as defined above, wherein the bacteriophage strain is further characterized and selected based on at least one of: b) characterizing toxin gene or antibiotic resistance gene or 16S RNA gene; and c) selecting is further based on at least one criteria selected from: absence of toxin gene; absence of antibiotic resistance gene; and absence of 16S RNA gene marker.

Particularly, the method comprises further characterizing the bacteriophage strain based on at least one of: b) temperature stability; stability at pH 4; and c) further selecting said characterized bacteriophage specie based on at least one criterion selected from: being stable at RT and/or pH 4.

According to a particular embodiment, the method further comprises: c) selecting at least two of the characterized strain based on: having different or complementary host ranges against at least 2 different bacterial strain; and d) combining the at least two selected bacteriophage strain to form a bacteriophage cocktail composition.

According to a particular embodiment of the method of the invention, the bacteriophage strain chosen for the prophylactic composition may be selected based on at least 3 or more criteria defined in step c). More particularly, the bacteriophage strain may be selected based on all criteria defined in step c).

In accordance with a particular embodiment of the present invention, the method as defined herein further comprising, in step d), combining at least 3 bacteriophage strains to form a bacteriophage cocktail composition. Alternatively, the method further comprises, in step d), combining at least 5 bacteriophage strains to form a bacteriophage cocktail composition.

Composition/Formulation/Cocktail

In accordance with a particular embodiment of the invention, there is provided the bacteriophage strain as defined herein and selected from the group consisting of: SEQ ID Nos: 1, 2,3, 4, 5, 6, 7, 8, 9, 10, 11, 12, 13, 14, 15, 16, 17, 18, 19, 20, 21, 22, 23, 24, 25, 26, 27 and 28. Particularly, the bacteriophage strain is selected from the group consisting of SEQ ID Nos: 9, 11, 13, 14, 21, 25 and 28.

Alternatively, the bacteriophage strains are defined by deposits filed at the International Canadian Depository Authority (IDAC) on Sep. 7, 2018, bearing numbers #: 070918-02; 070918-03; 070918-04; 070918-05 and 070918-06.

In accordance with a particular embodiment of the invention, there is provided a composition comprising at least one of the bacteriophages as defined herein, optionally in admixture with a physiologically acceptable carrier. Particularly, the physiologically acceptable carrier may be an excipient, such as water or a feed-compatible excipient.

In accordance with a particular embodiment, the bacteriophage of invention is suspended in a liquid. Alternatively, the composition is the bacteriophage is in dried form, such as a powder obtained after drying, such as for example, spray-drying or lyophilization.

In accordance with a particular embodiment of the invention, there is provided a cocktail composition comprising at least two bacteriophage strains as defined herein. Particularly, there is provided a bacteriophage cocktail comprising at least 2, 3, 4, 5, 6, 7, 8, 9, 10 or more bacteriophage strains as defined herein. More particularly, the cocktail composition comprises two, three, four or five or more bacteriophage strains as defined herein. Most particularly, the cocktail composition comprises five bacteriophage strains as defined herein.

Most particularly, the cocktail comprises at least two of the bacteriophage strains selected from the group consisting of SEQ ID Nos: 9, 11, 13, 14, 21, 25 and 28. Still, most particularly, the cocktail comprises all of the bacteriophage strains as defined by SEQ ID Nos: 9, 11, 14, 21 and 28.

Particularly, the cocktail of the present invention comprises bacteriophages having complementary host ranges against at least two different bacterial strains. More particularly, the cocktail comprises bacteriophages have complementary target specificity on at least two bacterial hosts.

Most particularly, the cocktail comprises bacteriophages directed against bacterial hosts that are selected from the group consisting of: APEC-A, APEC-B, APEC-C, APEC-D, APEC-E and APEC-F.

Alternatively, the cocktail comprises all bacteriophage strains deposited at the IDAC on Sep. 7, 2018, under numbers: 070918-02; 070918-03; 070918-04; 070918-05 and 070918-06.

In accordance with a particular embodiment, the present invention provides a formulation comprising the bacteriophage, composition or cocktail as defined herein, in admixture with a food, or feed or a food- or feed-acceptable carrier. Particularly, in the context of the present formulation, the carrier is water. Alternatively, the formulation is a food- or a feed-additive for livestock. Particularly, the formulation is in the form of a powder. Alternatively, the formulation is a food or a feed for livestock.

In accordance with a particular embodiment, the composition is formulated as a food or feed, and the carrier is a food- or feed-ingredient. Alternatively, the carrier is water, and the formulation is drinking-water for livestock.

In accordance with a particular embodiment, the composition is formulated as food- or feed-additive for livestock. Particularly, the preparation of the bacteriophage/composition/cocktail/formulation complies with strict safety requirements for food, feed, food- or feed-additives.

In accordance with a particular embodiment, there is provided a feed for livestock comprising anti-infection effective amount of the bacteriophage, composition, cocktail, or formulation, all as defined herein.

Method of Manufacture

In accordance with a further embodiment of the invention, there is provided a method of the manufacture of a feed for livestock comprising the step of: admixing the feed as defined herein with the bacteriophage/composition/cocktail/formulation as defined herein.

Uses

In accordance with a further embodiment of the invention, there is provided a use of the bacteriophage, composition, cocktail, or formulation as defined herein, for the prevention of opportunistic or pathogenic infections in livestock.

In accordance with an alternative embodiment of the invention, there is provided the bacteriophage, composition, cocktail of formulation as defined herein, for use in the prevention of opportunistic or pathogenic bacterial infections in livestock.

In accordance with an alternative embodiment, the present invention provides the use of at least one of the bacteriophage strains as defined herein for the manufacture of a composition for preventing opportunistic or pathogenic bacterial infections in livestock.

In accordance with an alternative embodiment, the present invention provides the use of at least two or more of the bacteriophage strains as defined herein for the manufacture of a cocktail for preventing bacterial infections in livestock.

Particularly, there is provided the use of the bacteriophage or cocktail as defined herein for the manufacture of a composition for preventing opportunistic or pathogenic bacterial infections in livestock.

In accordance with an alternative embodiment of the invention, there is provided a use of the bacteriophage as defined herein, or the composition as defined herein, or the formulation as defined herein, for the manufacture of a feed for livestock for preventing opportunistic or pathogenic infections in livestock.

Particularly, in accordance with the use, the bacteriophage is in the form of a powder, and the powder is mixed with foodstuff during the manufacture of feed, or the bacteriophage is added to the drinking water. Alternatively, the bacteriophage is in a liquid form, and the liquid is sprayed on foodstuff during the manufacture of feed, or the bacteriophage is added to the drinking water.

Method of Treatment

More particularly, there is provided a method for preventing an opportunistic or pathogenic bacterial infection in a livestock comprising administering a bacterial growth-inhibiting concentration of the bacteriophage/cocktail/composition/formulation (i.e. bacteriophage alone or in the form of a composition, a cocktail or a formulation) as defined herein to said livestock. Particularly, the administration is oral. Most particularly, the administration is carried out by way of drinking water, food or feed.

In accordance with a particular embodiment, the invention provided a method for preventing APEC infections in poultry comprising adding the bacteriophage/composition/cocktail/formulation as defined herein to drinking water or to feed for consumption by chicks.

In accordance with an alternative embodiment of the invention, there is provided a method for preventing APEC infections in poultry comprising orally administering an anti-infection effective amount of the bacteriophage/composition/cocktail/formulation to chicks by way of drinking water or feed.

In accordance with a further embodiment of the invention, there is provided a method for preventing APEC infections in poultry comprising orally administering to chicks the bacteriophage/composition/cocktail/formulation as defined herein, wherein the bacteriophage is in liquid phase and sprayed on chick's feed, or on the chicks themselves.

According to a further embodiment, the invention provides a method for preventing APEC infections in poultry comprising orally administering to chicks the bacteriophage/composition/cocktail/formulation as defined herein, wherein the bacteriophage is in powder form and is added to chick's feed during manufacture.

Opportunistic/Pathogenic Bacteria

According to a particular embodiment, the invention provides the method as defined herein, where the opportunistic bacterial infection being targeted is caused by bacteria selected from: *Salmonella enterica, Listeria monocytogenes, Escherichia coli, Campylobacter jejuni, Staphylococcus aureus* and *Clostridium perfringens*.

More particularly, the opportunistic bacterium is pathogenic, most particularly, the pathogenic bacterium is *E. coli* such as 0157:H7, still most particularly: an extra-intestinal pathogenic *E. coli* (ExPEC) or an Avian Pathogenic *E. coli* (APEC). Most particularly, the pathogenic bacteria prevented by the bacteriophage of this invention may be one or more of: APEC-A, APEC-B, APEC-C, APEC-D, APEC-E and APEC-F.

Livestock

Particularly, the livestock benefitting from this preventive/curative treatment is selected from: poultry, pigs, beef or veal. More particularly, the livestock is chicken, turkey or pigs. Most particularly, the livestock is a broiler chick from 1 to 34 days old.

Still, most particularly, the pathogenic bacteria stain is an APEC and the livestock is poultry, such as broiler chicks.

The following examples are put forth to provide those of ordinary skill in the art with a complete disclosure and description of how to make and use the present invention and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

EXAMPLES

Isolation, Purification, Characterization and Use of Phages Against E. Coli APEC The present examples describe the methods used to isolate environmental phages against the avian pathogenic Escherichia coli (APEC) and their use to prevent infection and losses in the poultry industry.

Example 1—Isolation of Bacteriophages

Concentration of the Phages from Environmental Samples

This step allows the concentrating of phages from environmental samples prior to the enrichment step that follows. To isolate the phages, 6-8 L environmental samples were collected from different environments (Beauport river [46°51'35.7"N 71°11'48.6"W; 46°52'02.0"N 71°12'34.8"W] from Beauport, and Boyer river [46°47'15.9"N 70°55'24.9"W] near Saint-Charles-de-Bellechasse). Big debris were removed from the sample using paper filters. Polyethylene glycol (PEG—M.W. 8000) and sodium chloride (NaCl) were added to the samples to a final concentration of 10% and 0.5M respectively. The samples were then incubated for 16 h at 4° C. with gentle agitation. The viral suspension was then centrifuged at 12,000 g for 15 min at 4° C. The supernatant was discarded, and the pellet, mainly composed of PEG 8000 and viruses, was gently resuspended in 4 mL of phage buffer (50 mM Tris-HCl pH7.5, 100 mM NaCl and 8 mM MgSO$_4$). Adding 10% of chloroform to the final suspension and incubating 16 h at 4° C. removed residual bacterial contamination to obtain viral concentrates.

ENRICHMENT OF PHAGES FROM THE CONCENTRATE

The enrichment step allowed increasing the concentration of viruses targeting selected bacterial strain.

First Enrichment

All work was carried out under biosafety level 2.

Bacterial strains (APEC A, B, C, D, E and F, etc.) were inoculated and incubated at 37° C. for 16 h on solid LB medium (per L of solid LB medium: 10 g of Bacto Tryptone, 5 g of yeast extract, 10 g of NaCl and 1% agar) the day prior to the enrichment. The day of the experiment, the bacterial strains were inoculated in 2 mL LB medium (per L of LB medium: 10 g of Bacto Tryptone, 5 g of yeast extract and 10 g of NaCl) and pre-incubated at 37° C.

The bacterial cultures were allowed to recover in fresh media by incubating the tubes at 37° C. for 1 h. In the meantime, the viral concentrates were centrifuged at 10 000×g for 10 min to separate the chloroform from the viral suspension. Only the upper phases were kept. Then, 2 mL of the phage concentrates were added to the bacterial culture and incubated 4 h at 37° C. If several bacterial strains were targeted, the concentrate was diluted to enable enrichments with the required number of strains. The first enrichments were kept at 4° C.

Second Enrichment

The targeted bacterial strains were inoculated in 2 mL of LB medium pre-incubated at 37° C. The bacterial cultures were allowed to recover in fresh media for 1 h at 37° C. In the meantime, the first enrichments were centrifuged at 10 000×g for 10 min to pellet remaining bacterial cells and debris. Then, 2 mL of the supernatants were added to the bacterial culture and the mix was incubated 4 h at 37° C.

Third Enrichment

The same steps described in the second enrichment were repeated. Between each enrichment, the phage titer was evaluated using the spot test method described below.

Titration of the Phages Using the Spot Test Assay

The spot test assay allowed rapid estimation of the phage titer in the enrichment steps and was designed for high-throughput screening. First, the bacterial strains were inoculated in 5 mL of sterile saline (0.85% NaCl) to obtain an optical density of 0.05-0.1 at 600 nm (O.D.$_{600\ nm}$). The cell suspensions were used to obtain a confluent bacterial lawn on solid LB medium. To do so, 2 mL of the suspension was deposited on the surface of a LB Petri dish. The suspension was allowed to spread and cover the entire surface of the medium. Then the excess culture was removed with a pipet and tilting the Petri allowed to remove most of the excess. The Petri were then dried close to an open flame for 30 min. This was repeated for each strain and several Petri dishes were prepared to titrate the enrichments on each strain (it is possible to titer 6 enrichments per Petri). One-hundred (100) μL of the enrichments was transferred into a 96 well plate according to the disposition shown in FIG. 1. Ninety-nine (99) μL of phage buffer was then transferred in rows B, C, D, F, G, and H. The enrichments were then diluted 1:99 μL by transferring 1 μL of the enrichments to 99 μL of phage buffer as shown in FIG. 1 (this can be done using a multichannel pipet P10).

Figure 2:
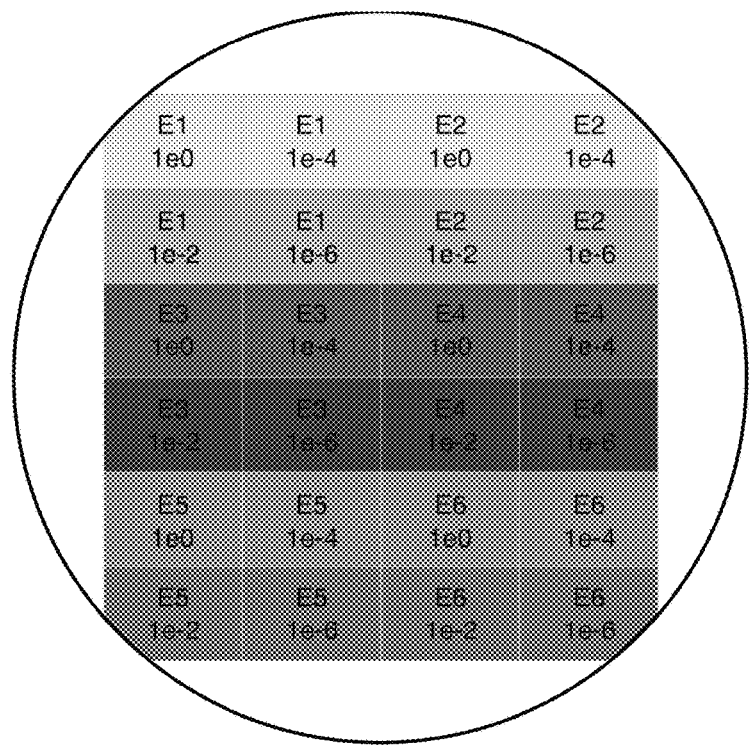
FIG. 2. Disposition of phage dilutions on Petri dish.

To deposit the dilutions on the Petri dish, a box of tips was prepared where each other row was kept empty. Then using the multichannel P100, 5 μL of the dilutions was taken from the plate, starting with B1, D1, F1 and H1 and the drop placed on the Petri dish previously inoculated with the selected bacterial strain according to the disposition shown in FIG. 2. Without changing tips, 5 μL of the dilutions A1, C1, E1 and G1 were taken and each drop placed on the Petri dish according to the disposition shown in FIG. 2. If the dilutions were to be tested against many strains, it was possible to use the electronic multichannel pipet P100 and dispense 5 μL of the dilutions rapidly on many Petri dishes.

The drops on the Petri were left to dry and be completely absorbed in the medium before incubation at 37° C. for 16 h.

When the phage titer reached 1e7 plaque forming units (PFU)/mL, enrichment was stopped, and the purification steps were undertaken as described in Example 2.

Example 2—Purification of Phages Against E. Coli APEC

Purification of Phages

If the titer of phages was high enough (>$10^5$ PFU/mL), the purification procedure was initiated. Purification of phages was carried out with a protocol very similar to the phage titration except that 8 dilutions of the same phage were tested instead of only 4. The phage enrichments were purified on each sensitive strain. This procedure allowed to obtain a single phage specie in solution instead of a mixed population.

First Round of Isolation

First the bacterial strains were inoculated in 5 mL of sterile saline (0.85% NaCl) to obtain an optical density of 0.05-0.1 at 600 nm (O.D.600 nm). The cell suspensions were used to obtain a confluent bacterial lawn on solid LB medium. To do so, 2 mL of the suspension were deposited on the surface of an LB Petri dish. The Petri was tilted to spread the liquid and cover the entire surface of the medium. Then the excess culture was removed with a pipet—tilting the Petri allowed removing most of the excess. The Petri dishes were then dried close to an open flame for 30 min. This was repeated for each strain and several Petri dishes were prepared, in sufficient numbers to make sure there was enough to titrate the enrichments on each strain to be tested (it is possible to titer 6 enrichments per Petri). Meanwhile, 100 μL of the enrichments were transferred into row A of a 96 well plate (again see FIG. 1 for disposition of the enrichments in the 96 well plate). Then, 90 μL of phage buffer were added in the remaining rows. Finally, the enrichments were serially diluted 1:9 to a final dilution factor of 1e-7.

Using the multichannel P100, 10 μL of the dilutions were deposited on the Petri dishes inoculated with the host strains, starting with B1, D1, F1 and H1. Wthout changing tips, 10 μL of the dilutions A1, C1, E1 and G1 were transferred on the same Petri. If the dilutions were tested against many strains, an electronic multichannel pipet P100 was used to dispense 10 μL of the dilutions on many Petri rapidly. The drops on the Petri dishes were left to dry and be completely absorbed in the medium before incubation at 37° C. for 16 h.

Second and Third Round of Isolation

Figure 7:
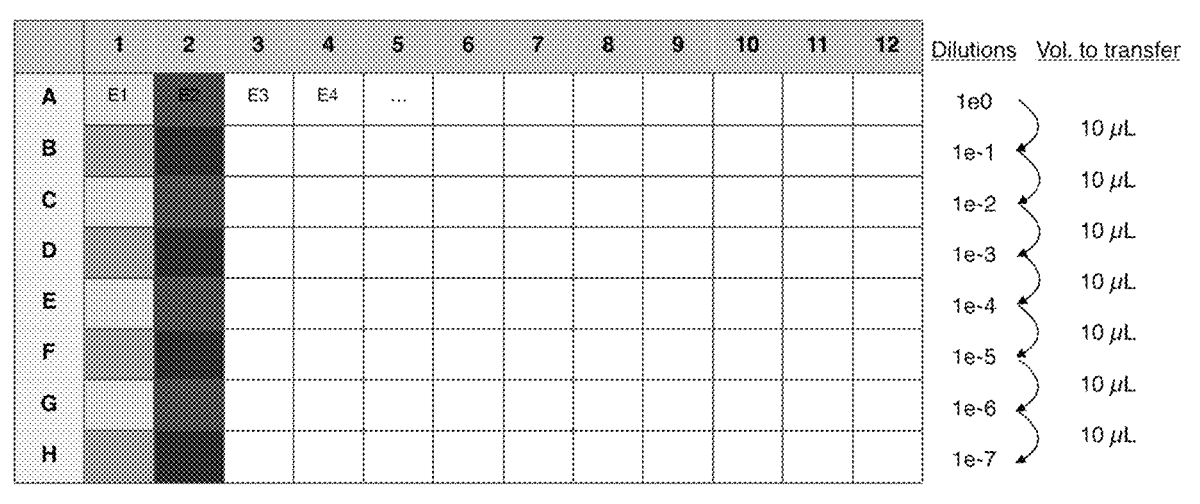

The bacterial lawns were prepared as previously described. Isolated lysis plaques were picked with a truncated pipet tip and transferred to row A of a 96 well plate that was previously filled with 90 μL of phage buffer. The lysis plaques were allowed to diffuse for 30 minutes at room temperature. The phage suspension was then serially diluted 1:9 to a final dilution factor of $10^{-7}$ and 10 μL of the dilutions were transferred on the bacterial lawn as previously described. The same protocol was repeated for the third round of isolation (FIG. 7).

First Amplification of the Purified Phages

After the last round of purification, the isolated lysis plaques were picked with a truncated tip and transferred in a 96 well plate that was previously filled with 200 μL of LB medium inoculated at 1% from an overnight culture of the bacterial host strain. The $OD_{600\ nm}$ was monitored in a plate reader set to incubate at 37° C. When lysis of the bacterial host was observed, the plaque was kept at 4° C. for the second amplification.

Second Amplification of the Purified Phages

The bacterial host strains were first inoculated at 1% in 5 mL of LB medium and incubated at 37° C. until the $O.D._{600\ nm}$ reached 0.1. Then 50 μL of the purified phages were added to the bacterial cultures and incubated until lysis. The phage lysates were centrifuged for 10 min at 5 000×g and filtered through 0.45 μM syringe filters before titration.

Example 3—Characterization E. Coli APEC Bacteriophages

Restriction Profile

The phages' DNA was isolated using standard protocol routinely used in phage research. Briefly, the phage lysates were treated with DNAse and RNAse to remove contaminating host nucleic and ribonucleic acids. Then the proteic capsid was destabilized with a strong detergent to release the viral genomic DNA. Proteins were then removed by precipitation with potassium acetate and centrifugation. Nonetheless, the supernatant still contained traces of proteins that was eliminated with a phenol-chloroform extraction, followed by an ethanol-precipitation of DNA. The final DNA pellet was dissolved in sterile distilled water.

Figure 3:
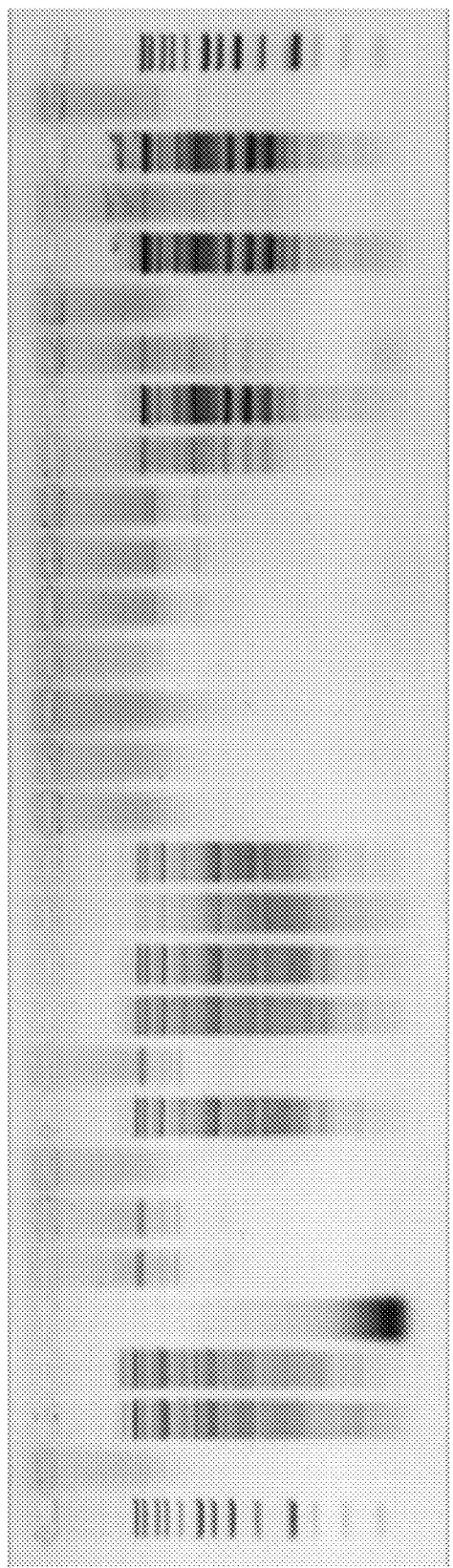
FIG. 3. Ssp1 restriction profile of bacteriophage strain.

The DNA concentration was verified by agarose gel electrophoresis and samples containing enough DNA were digested with restriction enzyme: BamH III or Ssp1. The restriction profile (FIG. 3) of the phages allowed visual identification of unique phages that were selected for further characterization.

Host Range

The host range was defined by the number of different bacterial strains a phage could infect. To determine the host range, a bacterial lawn was made as described previously. Then 200 μL of phage lysate was transferred in a 96 well plate and a multichannel pipet was used to transfer 2.5-3 μL of the lysate on the bacterial lawn. The Petri dishes were incubated at 37° C. for 16 h.

Figure 4:
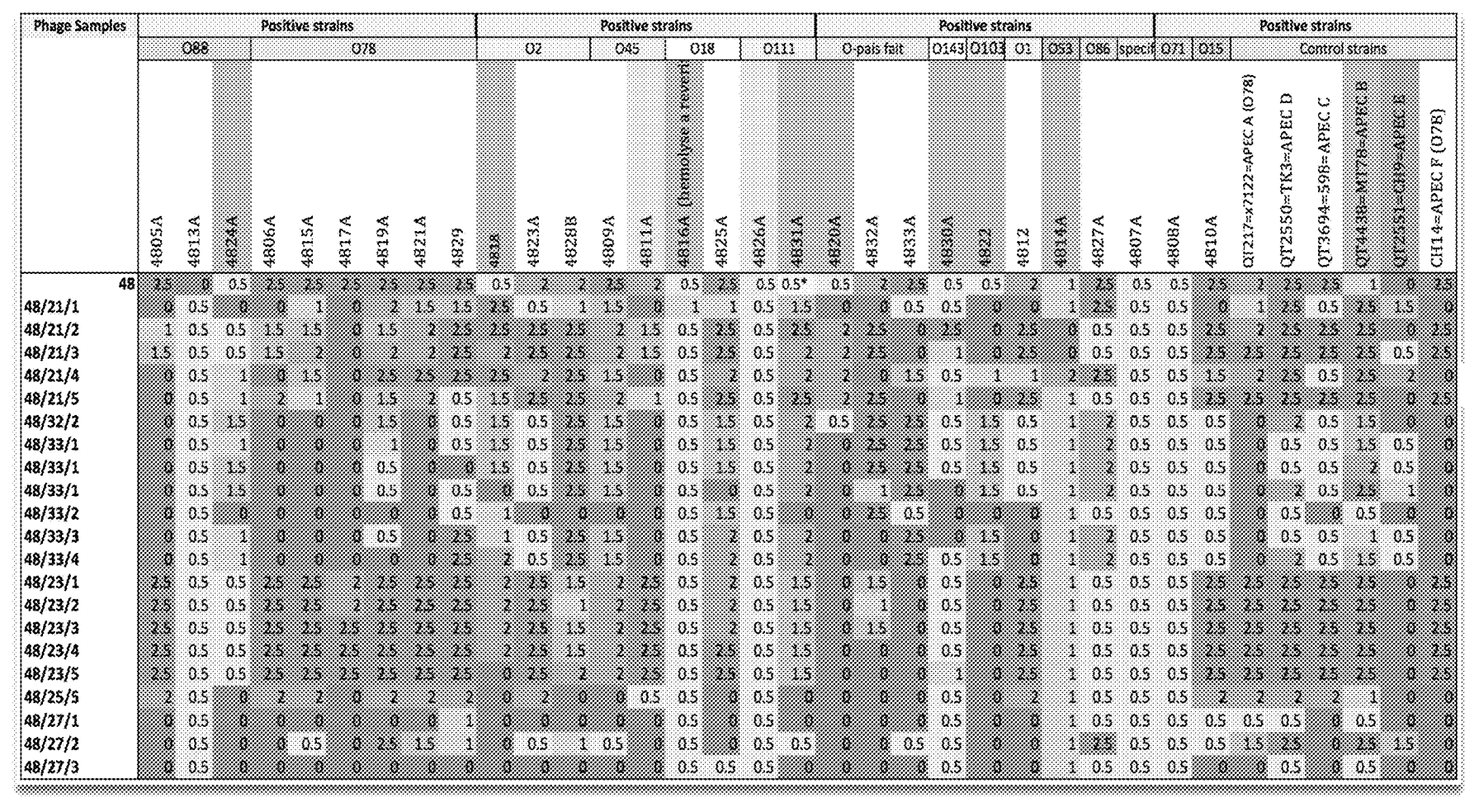

The lysis efficiency was measured on a scale of 0 to 3 (0: no lysis, 1: turbid lysis, 2: partial lysis; and 3 complete lysis). The results shown in FIGS. 4 and 5 demonstrate that the isolated phages are polyvalent and infect many problematic APEC strains isolated from the industry.

Phage Stability—pH

Figure 6:
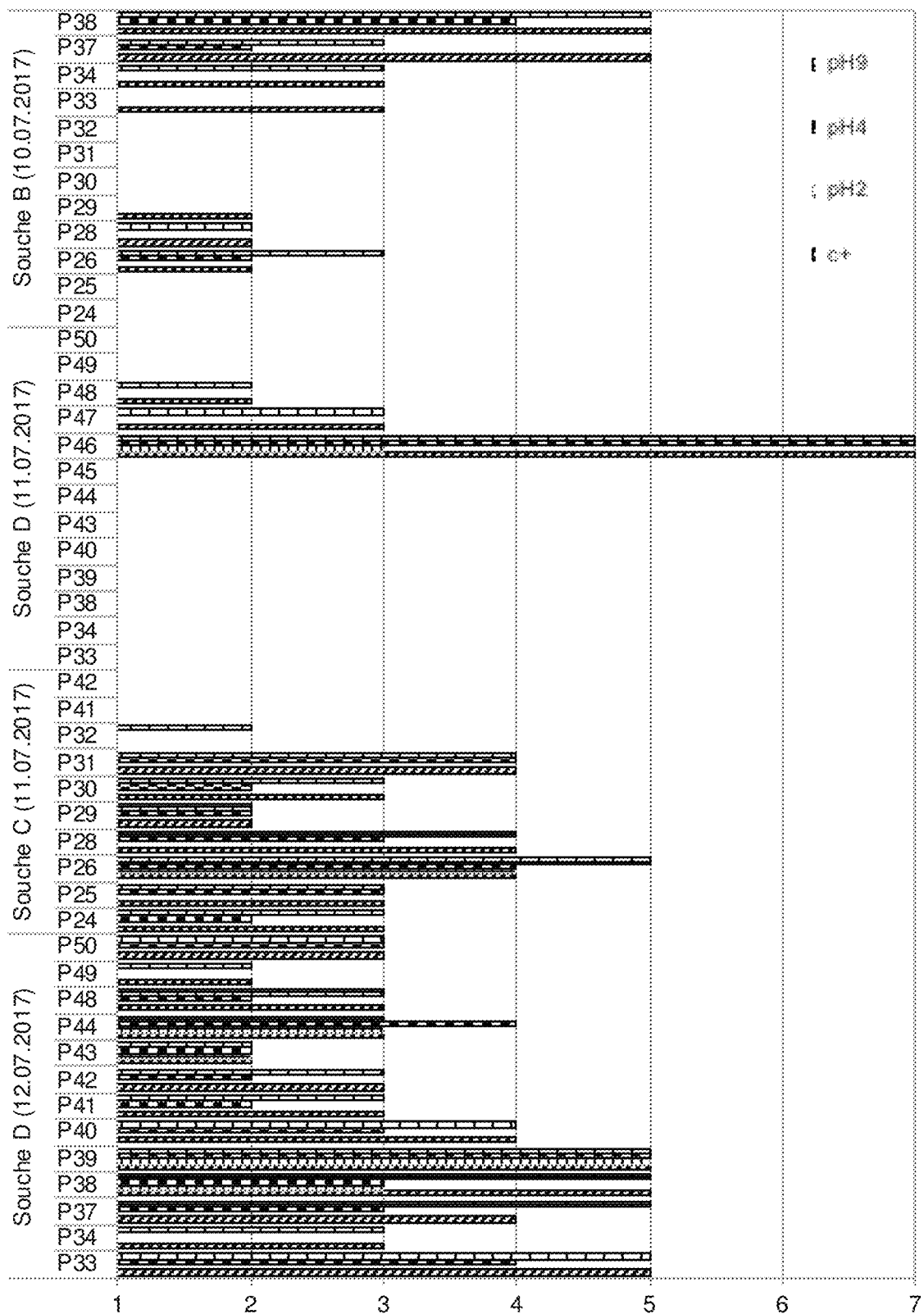
FIG. 6. Stability of the phages to different pH.

The stability of the phages at pH 2, 4 and 9 was tested. First, the pH of liquid LB medium was adjusted to the desired pH either with HCl or NaOH. Then the phages were diluted 1:9 in the acidic or basic LB medium and were incubated for 30 min at room temperature. Before titration, the pH of the medium was neutralized by diluting the treated phages in phage buffer (1:9). The results indicated that the majority of phages were stable at pH 4 and 9, whereas many were affected at pH 2 (FIG. 6).

Phage Stability—Shelf Life

To demonstrate the stability of the phages, samples are kept at 4° C. and at room temperature for more than 9 months. Periodical titrations of these samples reveal that the isolated phages are stable for more than 6 months at 4° C. and at room temperature.

Burst Size and Latency Time

After selecting the phages with different restriction profiles (FIG. 3), broad host range (FIGS. 4 and 5) and stability to acidic pH (FIG. 6), we measured the burst size of the phages. The burst size is a proxy of the virulence of a phage. It corresponds to the number of viruses released by an infected cell. Generally, an infected cell releases an average of 50-100 virions and we wanted to select the phages in our collection that had the highest burst size. Some phages infecting E. coli could have burst size greater than 1000.

To establish the burst size of the present phages, the bacterial host were infected with a phage specie to obtain a phage/host ratio of 5. This ensures that every cell in the culture is infected. The titer is measured at 10 minute-intervals for a total of 60 minutes. The burst size is then calculated by dividing the number of phages at the end of the infectious cycle by the initial number of phages.

Genome Sequence and Detection of Undesired Genes

Figure 8:
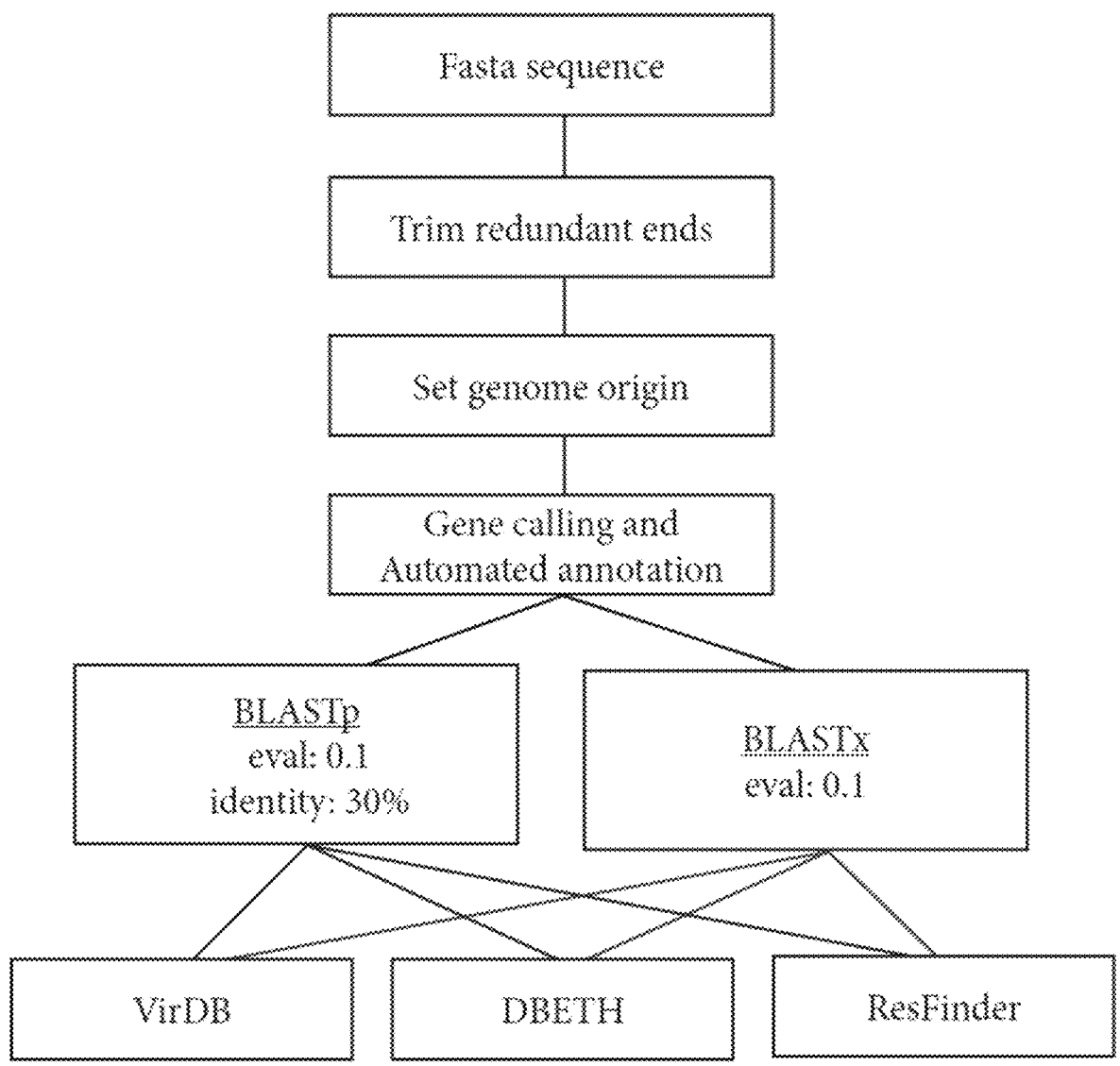
FIG. 8. Scheme illustrating the bioinformatics pipeline to screen the phage genomes.

The genome of the phages with the most interesting features (host range, stability to temperature or pH, burst size) were sequenced using Next Generation sequencing. The genome was assembled using Spades with the default settings. Once the genomes were assembled into one "contig", we verified if the contig had redundant ends. If the ends were redundant, it meant that the genome was complete and circular. Otherwise, more sequencing efforts were carried out for the completion of the genome. This was done using primer walking on the genome by sequencing PCR products, amplified using the phage genome as template. The redundant ends were removed from the complete phage genome using BLASTn and python scripts that aligned the end of the genome and removed the one redundant extremity (FIG. 8).

The coding sequences were detected using the software Genemark. Python scripts were used to convert the Genemark output in a Genbank compliant flat file from which the protein sequences were extracted. Finally, a bioinformatics analysis was carried out to detect the presence of undesired genes such as toxin, antibiotic resistance, 16S RNA and integrase coding genes (FIG. 8).

Toxin genes were identified by searching homologs of the phage's protein and DNA sequence in public databases of known toxins (VirDB and DBETH) and antibiotic resistance genes (ResFinderDB). Programs BLASTp and BLASTx were used to respectively analyze the protein and DNA sequences of each phage. This first step is sensitive but not specific, meaning that the E-value (expectation of error) is set to 0.1 (1 chance out of 10 of false positive). The data were then parsed to keep only alignments that shared more than 30% identity with toxin or antibiotic resistance genes and for which the alignment spanned more that 75% of the length of the longest protein sequence for protein/protein comparison (BLASTp), or more than 75% of the length of the homologous protein in the database for DNA/protein comparison (BLASTx).

Figure 9:
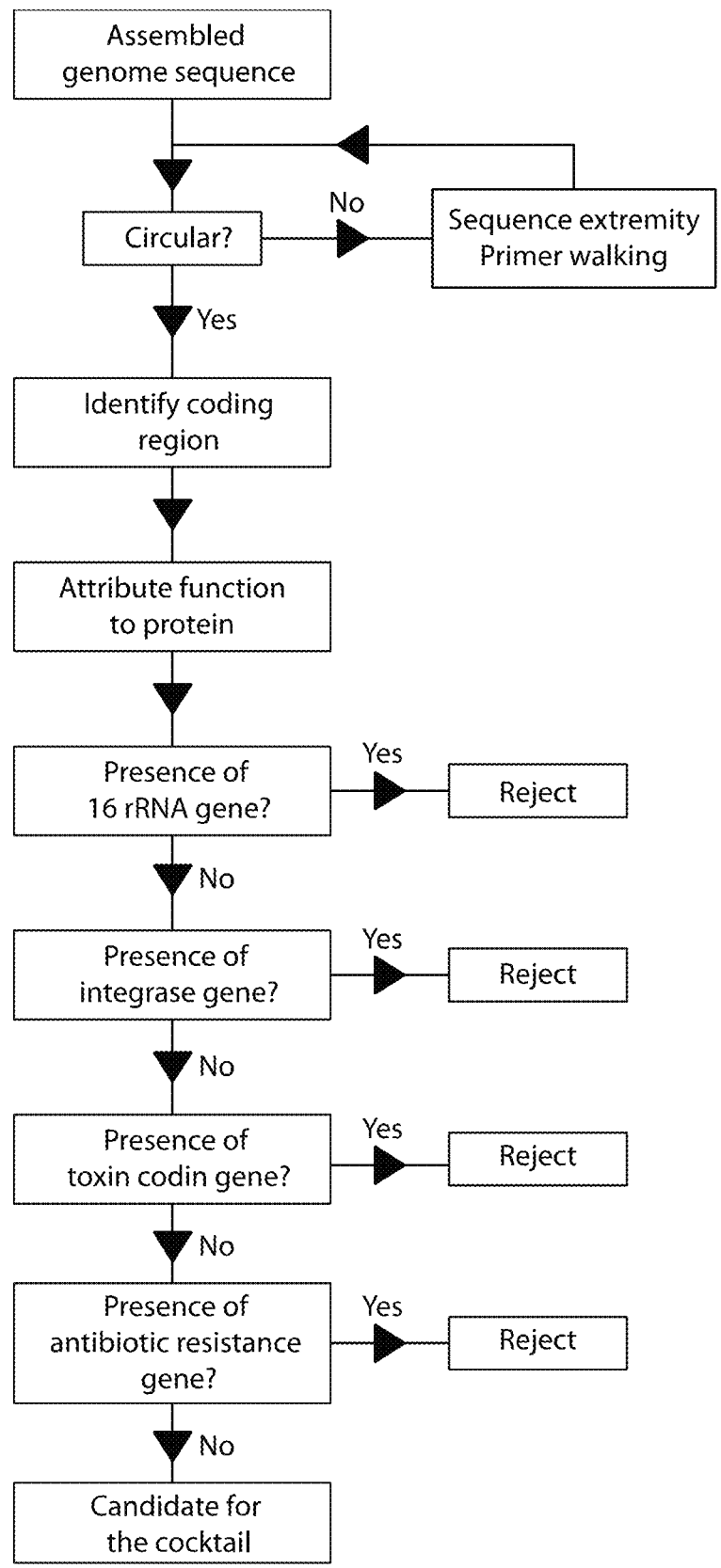
FIG. 9. Scheme illustrating the gene screening pipeline for decision-making in the selection of phages.

A detailed annotation of these phage genomes allowed to detect 16S and integrase coding genes. The translated coding sequences of the phages were compared to the NCBI GenBank database to identify homologous proteins for which the function was known. The program BLASTp was used with a threshold E-value of 1e-3. The top 5 hits were analysed and the function of the phage protein was extrapolated from the function that was previously attributed to these homologous proteins. Finally, we looked for conserved functional domains within our phage proteins to extend the functional annotation. We used InterProScan program and database to screen and detect conserved domains to confirm, infirm or attribute new functions to the phage proteins. This ensured a thorough annotation of the phage proteins and identification of 16S RNA and integrase coding genes. FIG. 9 illustrates the decision tree to keep or reject the phage based on sequence annotations.

The identified phages and their respective DNA sequences are listed in Table 1 and corresponding representative electron microscopy images are shown in FIGS. 12-21.

TABLE 1

Overview of the phage genome assemblies and morphology.

| Phage | Size | Coverage | Best Hits | Acc. number | Hit Size | Species | EM picture | SEQ ID NO. |
|---|---|---|---|---|---|---|---|---|
| 5a | 356230 | 173.289 | Escherichia phage vB_Eco_slurp01 genome assembly, chromosome: I | LT603033 | 348043 | Giant Phage | FIG. 12 | 27 |
| 11 | 354341 | 211.399 | Escherichia phage vB_Eco_slurp01 genome assembly, chromosome: I | LT603033 | 348043 | Giant Phage | FIG. 13 | 9 |
| 8a | 72689 | 753.93 | Escherichia phage vB_EcoP_PhAPEC7, complete genome | KF562340 | 71778 | Podoviridae; G7cvirus | FIG. 14 | 28 |

TABLE 1-continued

Overview of the phage genome assemblies and morphology.

| Phage | Size | Coverage | Best Hits | Acc. number | Hit Size | Species | EM picture | SEQ ID NO. |
|---|---|---|---|---|---|---|---|---|
| 35a | 72689 | 658.444 | *Escherichia* phage vB_EcoP_PhAPEC7, complete genome | KF562340 | 71778 | Podoviridae; G7cvirus | | 14 |
| 42b | 72689 | 49.4428 | *Escherichia* phage vB_EcoP_PhAPEC7, complete genome | KF562340 | 71778 | Podoviridae; G7cvirus | FIG. 15 | 19 |
| 43b | 72689 | 152.16 | *Escherichia* phage vB_EcoP_PhAPEC7, complete genome | KF562340 | 71778 | Podoviridae; G7cvirus | | 22 |
| 44a | 72689 | 41.5239 | *Escherichia* phage vB_EcoP_PhAPEC7, complete genome | KF562340 | 71778 | Podoviridae: G7cvirus | | 23 |
| 47b | 72689 | 16.38 | *Escherichia* phage vB_EcoP_PhAPEC7, complete genome | KF562340 | 71778 | Podoviridae; G7 cvirus | | 26 |
| 33a | 151263 | 47.4752 | *Escherichia* phage ESCO5, complete genome | KX664695 | 149312 | Myo, Distinct clade | | 12 |
| 42a | 150995 | 233.99 | *Escherichia* phage ESCO5, complete genome | KX664695 | 149312 | Myo, Distinct clade | | 18 |
| 43a | 150995 | 383.773 | *Escherichia* phage ESCO5, complete genome | KX664695 | 149312 | Myo, Distinct clade | FIG. 16 | 21 |
| 47a | 150995 | 431.442 | *Escherichia* phage ESCO5, complete genome | KX664695 | 149312 | Myo, Distinct clade | FIG. 17 | 25 |
| 26 | 167442 | 283.7 | Enterobacteria phage RB10, complete genome | KM606999 | 168401 | Myoviridae; Tevenvirinae; T4virus | FIG. 18 | 10 |
| 32 | 167496 | 329.818 | Enterobacteria phage RB10, complete genome | KM606999 | 168401 | Myoviridae; Tevenvirinae; T4virus | FIG. 19 | 11 |
| 39 | 45353 | 1047.35 | Enterobacteria phage K1-5, complete genome | AY370674 | 44385 | Podoviridae; Autographivirinae | | 17 |
| 33b | 43963 | 2452.6 | *Escherichia* virus AAPEc6, complete genome | KX279892 | 44559 | Podoviridae; Autographivirinae | FIG. 20 | 13 |
| 35b | 45597 | 187.416 | *Escherichia* virus AAPEc6, complete genome | KX279892 | 44559 | Podoviridae; Autographivirinae | | 15 |
| 42c | 43963 | 358.238 | Enterobacteria phage K1-5, complete genome | AY370674 | 44385 | Podoviridae; Autographivirinae | FIG. 21 | 20 |
| 44b | 43964 | 1356.68 | *Escherichia* virus AAPEc6, complete genome | KX279892 | 44559 | Podoviridae; Autographivirinae | | 24 |
| 38 | 72689 | 770.811 | *Escherichia* phage ECBP1 | YP_006908771.1 | ? | Podoviridae; G7 virus. | | 16 |
| phi7 | 164948 | | Enterobacteria phage vB_EcoM_IME340, complete genome | MH051916.1 | 165549 | Myoviridae; Tevenvirina: T4virus | | 8 |
| phi49-33-3 | 349740 | | *Escherichia* phage PBECO 4 | KC295538.1 | 348113 | Myoviridae | | 6 |
| phi3_2 | 134466 | | *Escherichia* phage PDX | MG963916.1 | 138427 | Myovirida; Vequintavirinae; unclassified V5virus | | 5 |
| phi3_1 | 170558 | | *Escherichia* phage vB_EcoM_NBG1 | MH243438.1 | 168869 | Myoviridae; Tevenvirina: Rb69virus | | 4 |
| phi18-21-5 | 351003 | | *Escherichia* phage PBECO 4 | KC295538.1 | 348113 | Myoviridae | | 3 |
| phi49-33-4 | 346671 | | *Escherichia* phage PBECO 4 | KC295538.1 | 348113 | Myoviridae | | 7 |

TABLE 1-continued

Overview of the phage genome assemblies and morphology.

| Phage | Size | Coverage | Best Hits | Acc. number | Hit Size | Species | EM picture | SEQ ID NO. |
|---|---|---|---|---|---|---|---|---|
| phi11_1 | 111711 | | *Salmonella* phage Stitch | KM236244 | 123475 | Siphoviridae; T5virus | | 1 |
| Phi11_2 | 58609 | | Enterobacteria phage 9g | KJ419279.1 | 56702 | Siphoviridae; No nagvirus. | | 2 |

Example 4—Cross-Resistance

One more factor to be considered when selecting phages to compose a cocktail is the cross-resistance of the target bacterial strains, i.e. if a bacterial strain becomes resistant to a phage, whether it will also become resistant to other phages comprised in the cocktail.

To investigate cross-resistance, we challenge a bacterial strain (ex. APEC A) with a phage (Ex. Vb_EcoM_SBL001 or SBL001). Using a high phage/bacteria ratio (also named MOI for Multiplicity of Infection) leads to selection of Bacteriophage Insensitive Mutant (BIM). These BIMs are variants that evolve from the initial APEC A strain that are selected with the phage SBL001. A typical MOI to achieve selection of BIMs is close to 1 (1 phage per bacterial strain). Thus, bacterial strain is grown to an $O.D._{600\ nm}$ of 0.1 which correspond to a bacterial concentration of approximately 2e7 PFU/mL and the phage is added to 500 μL of the bacterial culture to reach the 1:1 ratio. The mixture is spread on a Petri dish with LB medium 1% agar and the Petri dish is incubated 16 h at 37° C. The Petri dishes are examined for bacterial colonies that correspond to BIMs selected by the phages.

Ten colonies are picked and transferred to 10 mL of LB medium. After incubation at 37° C., the host range of the phages is tested against these new variants. If a different phage (vB_EcoM_SBL002 for instance) that was infecting this bacterial strain, no longer infects the BIMs, it strongly suggests that both phages SBL001 and SBL002 are using the same receptor at the surface of the bacterial cell. The combination of both SBL001 and SBL002 in the cocktail would not be recommended as the probability of BIM emergence is high. Thus, in the planning the phage cocktail, a cross-resistance scheme is established for all isolated phages.

When combining two or more of these phages, a broad spectrum of APEC strains is targeted (Table 2), hence limiting the chances of selecting spontaneous mutants to less than one event per 1E9 to 1E10 generations.

Representative selected phages were deposited at the International Depositary Authority of Canada on Sep. 7, 2018, under the following numbers: 070918-02; 070918-03; 070918-04; 070918-05 and 070918-06. The phages selected for a first cocktail and their respective DNA sequences are listed in Table 2 Table 3, and corresponding representative electron microscopy images are shown in FIGS. 13, 14, 16, and 19.

TABLE 3

List of phages selected for a first cocktail
Example 5-Production and concentration of the phages

| Phage Strain | | EM picture | SEQ ID NO. | IDAC number |
|---|---|---|---|---|
| 8a | Podoviridae; G7cvirus | FIG. 14 | 28 | 070918-02 |
| 11 | Giant Phage | FIG. 13 | 9 | 070918-03 |
| 32 | Myoviridae; Tevenvirinae; T4virus | FIG. 19 | 11 | 070918-04 |
| 35a | Podoviridae; G7cvirus | | 14 | 070918-05 |
| 43a | Myo, Distinct clade | FIG. 16 | 21 | 070918-06 |

Example 5—Production and Concentration of the Phages

The bacteriophages are produced in 10 L fermenters. The day before, the bacterial seed culture is inoculated in 1 L of 2xYT media and incubated in 2 L flask at 37° C. on an orbital shaker set at 250 RPM. The fermenter vessel is prepared as per the manufacturer's recommendation (BioFlo 320—Eppendorf) and is filled with 10 L of sterile 2xYT media. The fermenter is inoculated with 500 mL of the seed culture. The auto culture mode is used for the optimal growth of *E. coli* until it reaches an $OD_{600\ nm}$ of 5. Then the agitation speed is reduced to a maximum of 250 RPM and

TABLE 2

List of host APECs targeted by the cocktail

| Phage (SEQ ID NO.) | APEC targets | | | | | | |
|---|---|---|---|---|---|---|---|
| | APEC-A | APEC-B | APEC-C | APEC-D | APEC-E | APEC-F | Poulvac |
| 8a (28) | 0 | 3 | 0 | 3 | 3 | 0 | 0 |
| 11 (9) | 0 | 2 | 3 | 0 | 0 | 0 | 0 |
| 32 (11) | 3 | 3 | 3 | — | 0 | 3 | — |
| 35a (14) | 0 | 3 | 0 | 3 | 0 | 0 | 0 |
| 43a (21) | 3 | 2 | 0 | 1 | 2 | 0 | 3 |
| 47a (25) | 3 | — | 0 | 1 | 3 | 0 | 3 |
| 33b (13) | 2 | 3 | 0 | — | 3 | 0 | 3 |

0: no lysis, 1: turbid lysis, 2: partial lysis; and 3 complete lysis.

phage is added to obtain a MOI of 0.01. The fermentation is carried on until complete lysis of the culture.

The lysate is first clarified using a 1 μm prefiltration step. Then the phages are purified using a two steps tangential flow filtration (Centramate-PaII). The first step uses 0.45 μm pore membranes that remove the bacterial debris and any remaining living cells. The phages are found in the filtrate. The second step uses 100 kDa pore-size membranes that retain the phages and allows concentration of the lysate. We concentrate the phage at least 10× to obtain high titers. Finally, the phage is diluted 10× with sterile saline (0.85% NaCl) and is concentrated again. This last step allows dilution of the 2xYT media, to be replaced by saline.

Example 6—Preparation of Phage Powder by Spray-Drying

Figure 10:
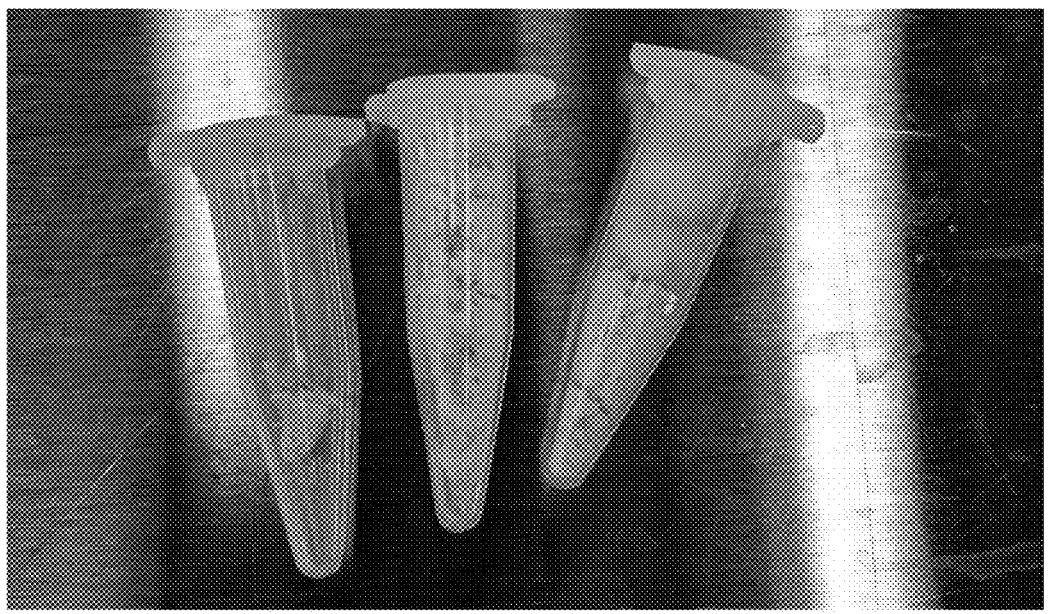
FIG. 10. Picture of the phage powder obtained after spray-drying.

First, lactose was added to the concentrated phage suspension for a final concentration of 2%. The phage suspension was then spray-dried using a mini spray-dryer Büchi-290. The suspension was fed at a constant feed rate 1.8-2.0 mL/min and an atomising airflow of 742 L/h with an aspiration rate of 35 m$^3$/h. The drying inlet air was heated to 62-65° C. and the outlet temperature ranged between 49-52° C. FIG. 10 shows the powder obtained.

Example 7—In-Vivo Investigation of the Effect of the Bacteriophage Preparation on Broiler Chicks—Laboratory-Scale Experiment This assay included 6 groups of chicks: A1) contaminated with *E. coli* X-A7122; A2) contaminated with *E. coli* X-A7122 and treated with phages; B1) contaminated with *E. coli* CM138; B2) contaminated with *E. coli* CM138 and treated with phages; C1) contaminated with *E. coli* MT78; C2) contaminated with *E. coli* MT78 and treated with phages. The respective concentration of the several (i.e. two to seven, or more) bacteriophages comprised in the cocktail was adjusted to 1e8 PFU/ml. Then, the phages were mixed by adding an equal volume of each in a mixing vessel. The phage cocktail was mixed to grounded feed. The mash was administered to the treated group with truncated pipet tip on day 1. The chicks of all groups were then contaminated with 1e8 CFU with the *E. coli* strains stated above. The bacterial strains were beforehand genetically modified and selected for nalidixic acid resistance allowing specific enumeration of these strains within the microbial community. None of the commensal strains were found to be resistant to this antibiotic marker.

Figure 11:
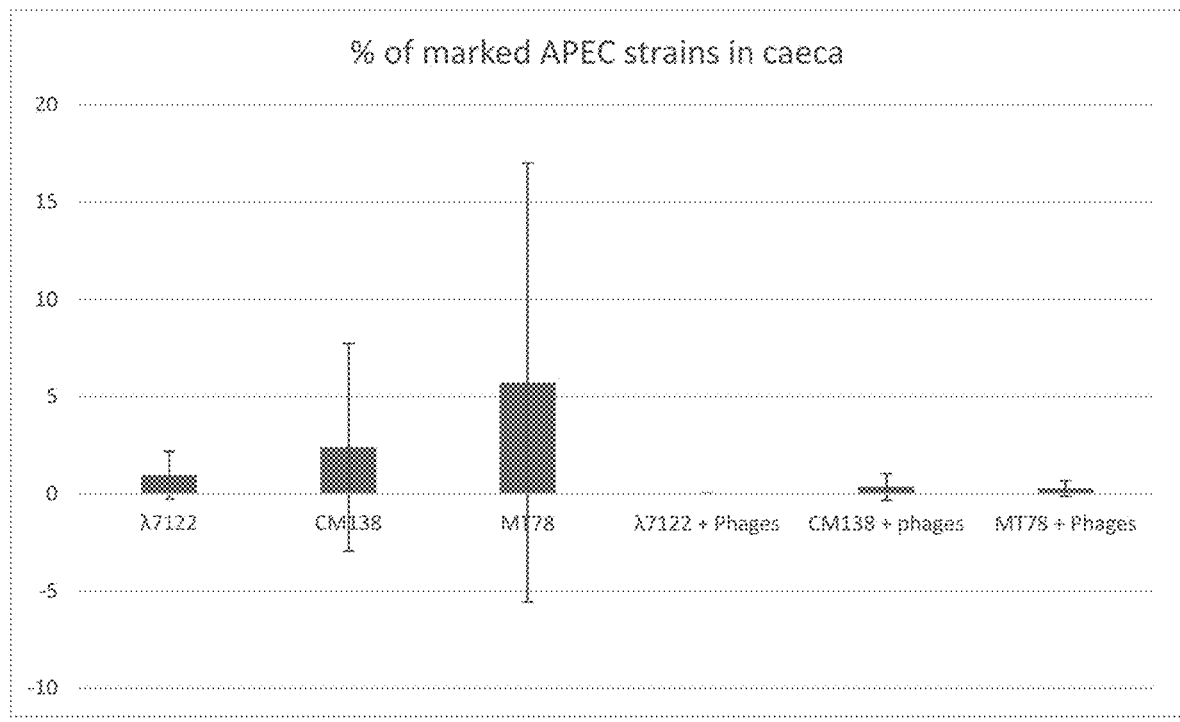
FIG. 11. Efficiency of elimination of *E. coli* by phages in laboratory-scale assay on chicken.
Figure 12:
FIG. 12. Representative electron microscopy image of phage 5a (SEQ ID NO: 27).
Figure 13:
FIG. 13. Representative electron microscopy image of phage 11 (SEQ ID NO: 9).
Figure 14:
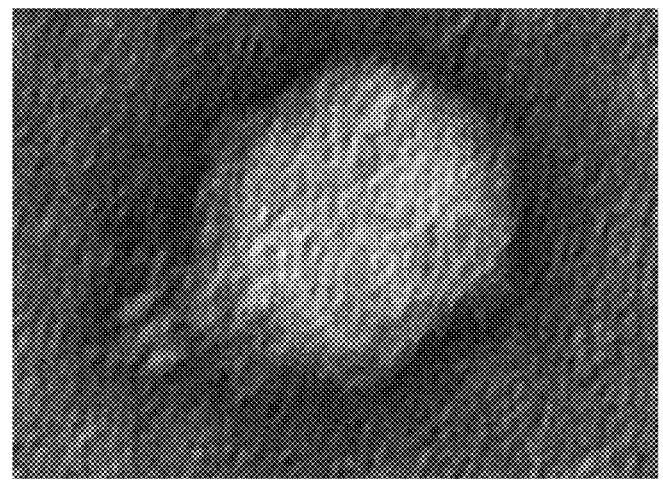
FIG. 14. Representative electron microscopy image of phage 8a (SEQ ID NO: 28).
Figure 15:
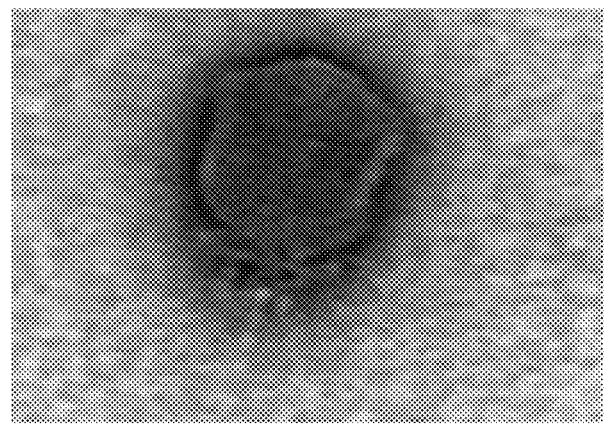
FIG. 15. Representative electron microscopy image of phage 42b (SEQ ID NO: 19).
Figure 16:
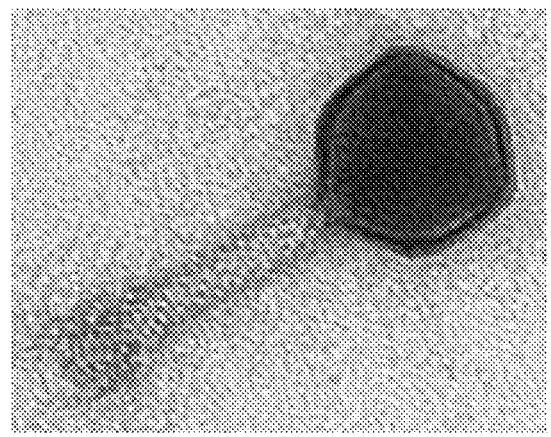
FIG. 16. Representative electron microscopy image of phage 43a (SEQ ID NO: 21).
Figure 17:
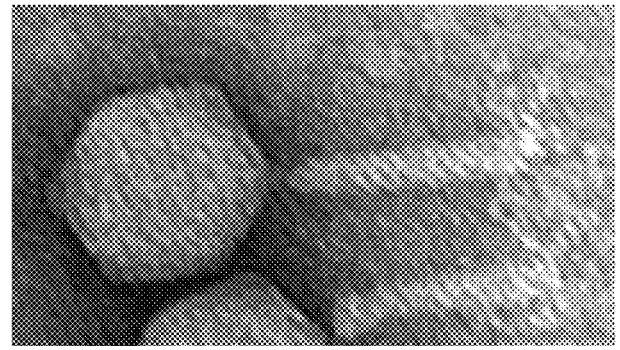
FIG. 17. Representative electron microscopy image of phage 47a (SEQ ID NO: 25).
Figure 18:
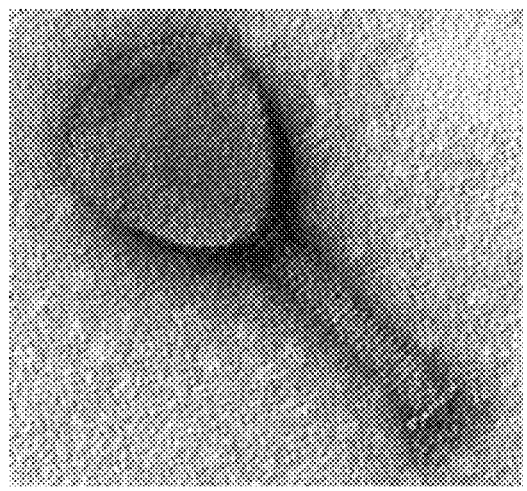
FIG. 18. Representative electron microscopy image of phage 26 (SEQ ID NO: 10).
Figure 19:
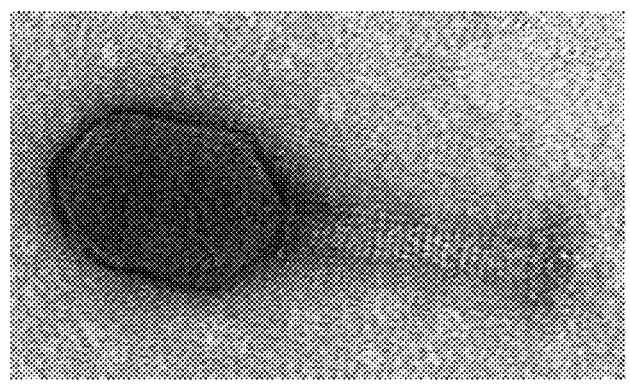
FIG. 19. Representative electron microscopy image of phage 32 (SEQ ID NO: 11).
Figure 20:
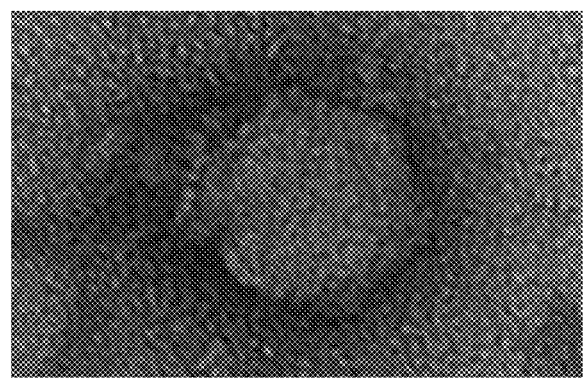
FIG. 20. Representative electron microscopy image of phage 33b (SEQ ID NO: 13).
Figure 21:
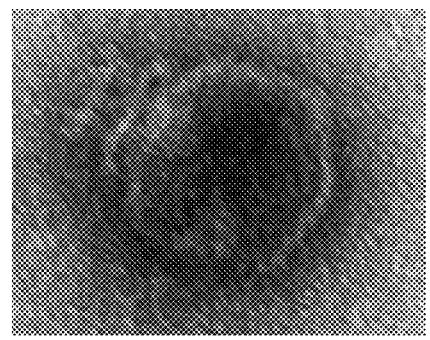
FIG. 21. Representative electron microscopy image of phage 42c (SEQ ID NO: 20).

We observed a reduction of the APEC strains titer in the caeca in the treated groups compared with the untreated groups showing the efficiency of the treatment (FIG. 11).

Example 8—In-Vivo Investigation of the Effect of Bacteriophage Preparation on Broiler Chicks—Field-Scale Experiment The respective concentration of the several (i.e. two to seven, or more) bacteriophages comprised in the cocktail is adjusted to 1e10 PFU/g. Then, the phages are mixed by adding an equal quantity of each powder in the mixing vessel. The phages are used as an additive in the starter-feed. The phage powder is added (400g/ton) to the starter-feed before conditioning and pelleting.

Kr-APEC is administered to the broilers from age 1 to 14-20 days in the starter-feed accordingly to the feeding schedule of the breeders. This in-vivo experiment comprises at least 12 flocks of 20,000 broilers divided into two groups. Control flock A is not treated, and flock B is treated with phages as described previously. Both flocks are bred in the same condition in different buildings. The carcasses of the dead broilers are collected, and post-mortem analysis are conducted to identify macroscopic colibacillosis-like lesions (perihepatitis, pericarditis, aerosac-culitis, enteritis). The number of broilers dead from colibacillosis in the control flock A is compared to the number of cases in the phage-treated flock B. Upon slaughter, 500-1000 birds of both groups are randomly selected for examination to identify colibacillosis-like lesions. The statistical significance of the results is examined using a one-way analysis of variance (ANOVA).

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. All such modifications are intended to be included within the scope of the appended claims.

All publications and patent applications cited in this specification are herein incorporated by reference as if each individual publication or patent application were specifically and individually indicated to be incorporated by reference.

REFERENCES

Costa et al., *Veterinary Microbiology* (2012), 160, 488-90.
Saini et al., *Journal of Dairy Science* (2012), 95, 4319-3.
Summers, *Annual Review of Microbiology* (2001), 55:437-51.
Huff et al., *Avian Diseases* (2003), 47:1399-1405.
Johnson et al., *Animal Health Research Review* (2008), 9:201-15.
Clark and March, *TRENDS Biotechnology* (2006), 24:212-18.
Kutter et al., *Current Pharmaceutical Biotechnology* (2012), 11:69-86.

---

SEQUENCE LISTING

The patent contains a lengthy sequence listing. A copy of the sequence listing is available in electronic form from the USPTO web site (https://seqdata.uspto.gov/?pageRequest=docDetail&DocID=US11872256B2). An electronic copy of the sequence listing will also be available from the USPTO upon request and payment of the fee set forth in 37 CFR 1.19(b)(3).

The invention claimed is:

1. A method for manufacturing a bacteriophage cocktail comprising at least two bacteriophage strains for the prevention of an opportunistic bacterial infection caused by pathogenic bacterial cells in livestock, the method comprising:
   a) characterizing at least two bacteriophage strains based on:
      (i) an absence of a gene encoding an integrase;
      (ii) an absence of a 16s rRNA gene marker;
      (iii) an absence of a gene encoding a human toxin;
      (iv) an absence of an antibiotic resistance gene;
      (v) a burst size greater than 10 against said pathogenic bacterial cells;
      (vi) stability at pH 4;
      (vii) stability at a temperature between 4° C. and room temperature (RT); and
      (viii) an absence of cross-resistance by said pathogenic bacterial cells against at least two bacteriophage strains by:
         providing a first and a second bacteriophage strain that infect the Pathogenic bacteria, the second bacteriophage strain being different from the first bacteriophage strain;
         culturing the first bacteriophage strain in the presence of said pathogenic bacteria at a Multiplicity of Infection (MOI) of at least about 1 until said bacteria develop resistance to the first bacteriophage strain, thereby producing a Bacteriophage Insensitive Mutant (BIM) pathogenic bacterial strain;
         challenging the BIM pathogenic bacterial strain with the second bacteriophage strain; and
         determining the absence of cross-resistance when the second bacteriophage strain still inhibits the growth of the BIM pathogenic bacterial strain; and
   b) selecting at least two bacteriophage strains characterized based on each of (i)-(viii) in step a), and combining to form the cocktail.

2. The method of claim 1, wherein the opportunistic bacterial infection caused by the pathogenic bacterial cells is selected from the group consisting of: *Salmonella enterica, Listeria monocytogenes, Escherichia coli, Campylobacter jejuni, Staphylococcus aureus* and *Clostridium perfringens*.

3. The method of claim 1, comprising selecting at least three bacteriophage strains.

4. The method of claim 1, comprising selecting at least four bacteriophage strains.

5. The method of claim 1, comprising selecting at least five bacteriophage strains.

6. The method of claim 1, wherein the at least two bacteriophage strains are further characterized in that they have different host ranges against at least two different pathogenic bacteria causing opportunistic bacterial infections.

7. The method of claim 1, wherein the at least two bacteriophage strains are further characterized in that they have complementary host ranges against at least two different pathogenic bacteria causing infections.

8. The method of claim 1, wherein the opportunistic bacterial infection is caused by an extra-intestinal pathogenic Escherichia coli (ExPEC) or an Avian Pathogenic *E. coli* (APEC).

9. The method of claim 1, wherein the at least two bacteriophage strains comprise a sequence selected from the group consisting of: SEQ ID NO: 1, 2, 3, 4, 5, 6, 7, 8, 9, 10, 11, 12, 13, 14, 15, 16, 17, 18, 19, 20, 21, 22, 23, 24, 25, 26, 27 and 28.

10. The method of claim 1, wherein the at least two bacteriophage strains are defined by the deposits filed at the International Canadian Depository Authority (IDAC) on Sep. 7, 2018 and bearing numbers #: 070918-02; 070918-03; 070918-04; 070918-05 and 070918-06.

11. The method of claim 1, wherein the bacteriophages have complementary host ranges against at least two different bacterial strains selected from the group consisting of: Avian Pathogenic Escherichia coli (APEC)-A, APEC-B, APEC-C, APEC-D, APEC-E and APEC-F.

12. The method of claim 1, wherein the livestock is poultry or pigs.

13. A formulation comprising a bacteriophage cocktail comprising at least two bacteriophage strains for the prevention of an opportunistic bacterial infection caused by pathogenic bacterial cells in livestock, in admixture with a food, a feed, or a food- or feed-acceptable carrier, wherein at least one of the bacteriophage strains comprises a sequence selected from the group consisting of: SEQ ID NO: 1, 2, 3, 4, 5, 6, 7, 8, 9, 10, 11, 12, 13, 14, 15, 16, 17, 18, 19, 20, 21, 22, 23, 24, 25, 26, 27 and 28, wherein the cocktail is in the form of a powder, and wherein the carrier is a food- or a feed-compatible excipient.

14. The formulation of claim 13, wherein the at least two bacteriophage strains comprise a sequence selected from the group consisting of: SEQ ID NO: 1, 2, 3, 4, 5, 6, 7, 8, 9, 10, 11, 12, 13, 14, 15, 16, 17, 18, 19, 20, 21, 22, 23, 24, 25, 26, 27 and 28.

15. The formulation of claim 13, being a food or a feed for livestock, wherein said livestock is poultry or pigs.

16. A formulation comprising a bacteriophage cocktail comprising at least two bacteriophage strains for the prevention of an opportunistic bacterial infection caused by pathogenic bacterial cells in livestock, in admixture with a food, a feed, or a food- or feed-acceptable carrier, wherein at least one of the bacteriophage strains is selected from the deposits filed at the International Canadian Depository Authority (IDAC) on Sep. 7, 2018 and bearing numbers #: 070918-02; 070918-03; 070918-04; 070918-05 and 070918-06, wherein the cocktail is in the form of a powder, and wherein the carrier is a food- or a feed-compatible excipient.

17. The formulation of claim 16, wherein the at least two bacteriophage strains are selected from the deposits filed at the International Canadian Depository Authority (IDAC) on Sep. 7, 2018 and bearing numbers #: 070918-02; 070918-03; 070918-04; 070918-05 and 070918-06.

18. The formulation of claim 16, being a food or a feed for livestock, wherein said livestock is poultry or pigs.

* * * * *